US010005715B2

(12) United States Patent
Siddiqui

(10) Patent No.: US 10,005,715 B2
(45) Date of Patent: Jun. 26, 2018

(54) METHOD FOR REMOVING DYE COMPOUNDS FROM AN AQUEOUS SAMPLE USING A FUNCTIONALIZED ASPHALTENE

(71) Applicant: King Fahd University of Petroleum and Minerals, Dhahran (SA)

(72) Inventor: Mohammad Nahid Siddiqui, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 358 days.

(21) Appl. No.: 14/949,928

(22) Filed: Nov. 24, 2015

(65) Prior Publication Data

US 2017/0144897 A1     May 25, 2017

(51) Int. Cl.
*C02F 1/28* (2006.01)
*C07C 205/00* (2006.01)
*C02F 101/30* (2006.01)

(52) U.S. Cl.
CPC .......... *C07C 205/00* (2013.01); *C02F 1/286* (2013.01); *C02F 2101/308* (2013.01); *C02F 2303/16* (2013.01)

(58) Field of Classification Search
CPC .... C02F 1/285; C02F 1/286; C02F 2101/308; C02F 2303/16; C07B 41/02; C07B 41/06; C07B 41/08; C07C 205/00; C07C 205/49; C07C 211/00; C07D 221/18; B01J 20/20; B01J 20/205; B01J 20/22; B01J 20/24; B01J 20/28007; B01J 20/28059; B01J 20/3085; B01J 20/3425; B01J 20/3475
See application file for complete search history.

(56) References Cited

U.S. PATENT DOCUMENTS

| | | | |
|---|---|---|---|
| 3,098,094 A * | 7/1963 | Pitchford | C07C 205/49 |
| | | | 106/284.4 |
| 9,212,159 B1 * | 12/2015 | Siddiqui | C07D 333/76 |
| 2016/0075567 A1 * | 3/2016 | Tour | C02F 1/001 |
| | | | 210/682 |

FOREIGN PATENT DOCUMENTS

| | | |
|---|---|---|
| CN | 103586001 A | 2/2014 |
| CN | 103623783 A | 3/2014 |
| WO | WO 2005/058482 A1 | 6/2005 |

OTHER PUBLICATIONS

El-Amin et al, The removal of Phenol and Its Derivatives from Aqueous Solutions by Adsorption on Petroleium Asphaltene, Jul. 2013 [online], [retrieved on Nov. 8, 2017]. Retrieved from the internet <URL:https://www.hindawi.com/journals/jchem/2013/694029/>.*

(Continued)

*Primary Examiner* — Matthew O Savage
(74) *Attorney, Agent, or Firm* — Oblon, McClelland, Maier & Neustadt, L.L.P.

(57) ABSTRACT

A functionalized asphaltene, obtained by refluxing with an acid solution. The functionalized asphaltene contains elevated levels of oxygen content due to nitration and oxidation of the refluxing process. The refluxing process also imparts organic functional groups including at least amines, nitro groups carbonyl groups, carboxylic groups and hydroxyl groups to the functionalized asphaltene, and these functional groups are attached to, thereby coating the surface of a functionalized asphaltene particle. A method for removing dye compounds from an aqueous sample with the functionalized asphaltene is also described.

14 Claims, 17 Drawing Sheets

(56) References Cited

OTHER PUBLICATIONS

Adam et al, The Removal of Phenol and Its Derivatives from Aqueous Solutions by Adsorption on Petroleum Asphaltene, Jul. 2013 [online], [retrieved on Nov. 8, 2017]. Retrieved from the internet <URL: https://www.hindawi.com/journals/jchem/2013/694029/>.*

John W. Shirokoff, et al., "Characterization of the Structure of Saudi Crude Asphaltenes by X-ray Diffraction", Energy & Fuels, vol. 11, No. 3, 1997, pp. 561-565.

Misbah-ul-Hasan, et al., "Separation and characterization of asphaltenes from Saudi Arabian crudes", Fuel, vol. 67, Aug. 1988, pp. 1131-1134.

* cited by examiner

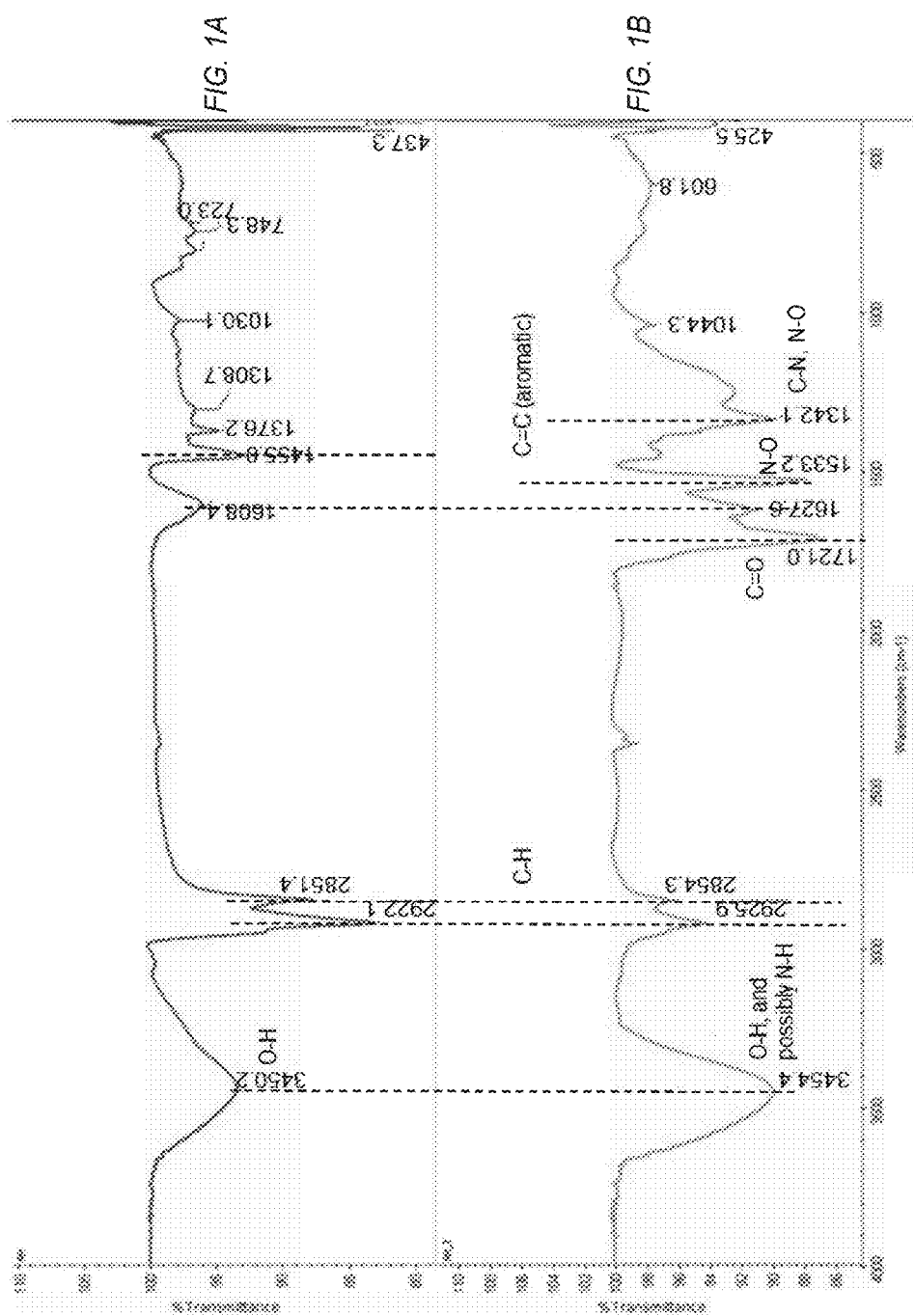

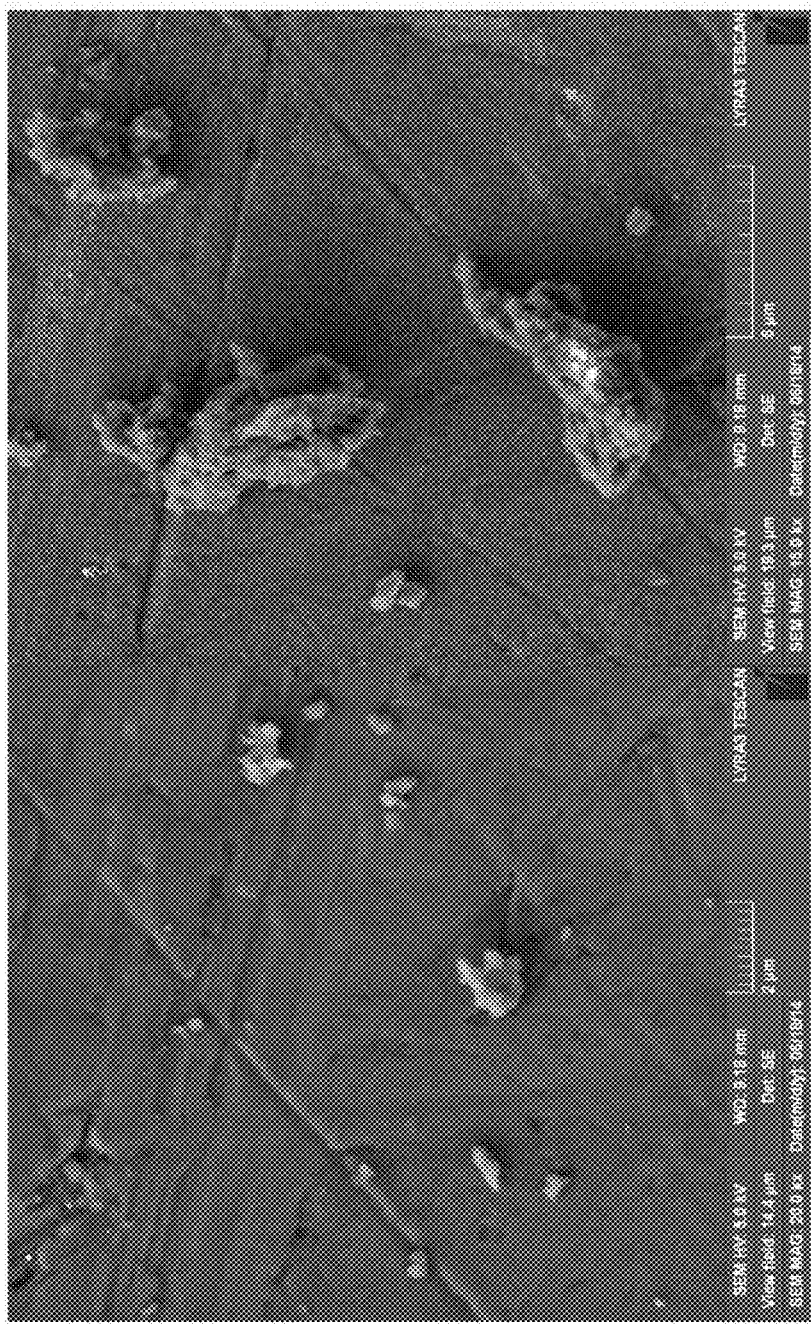

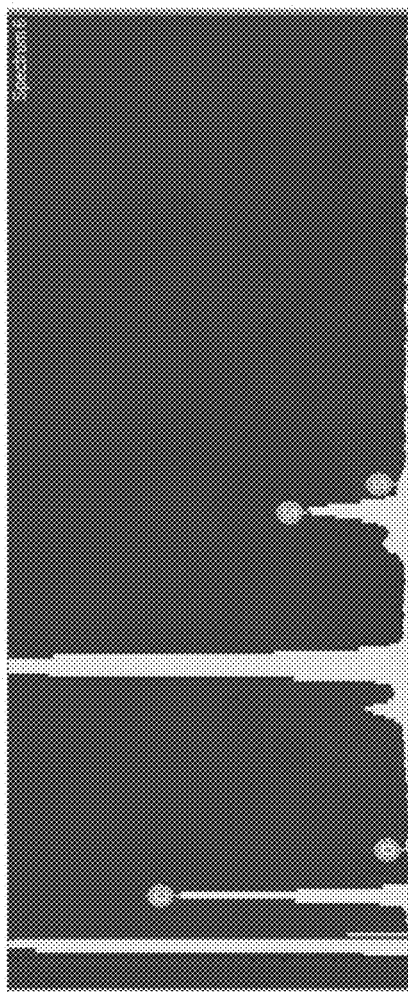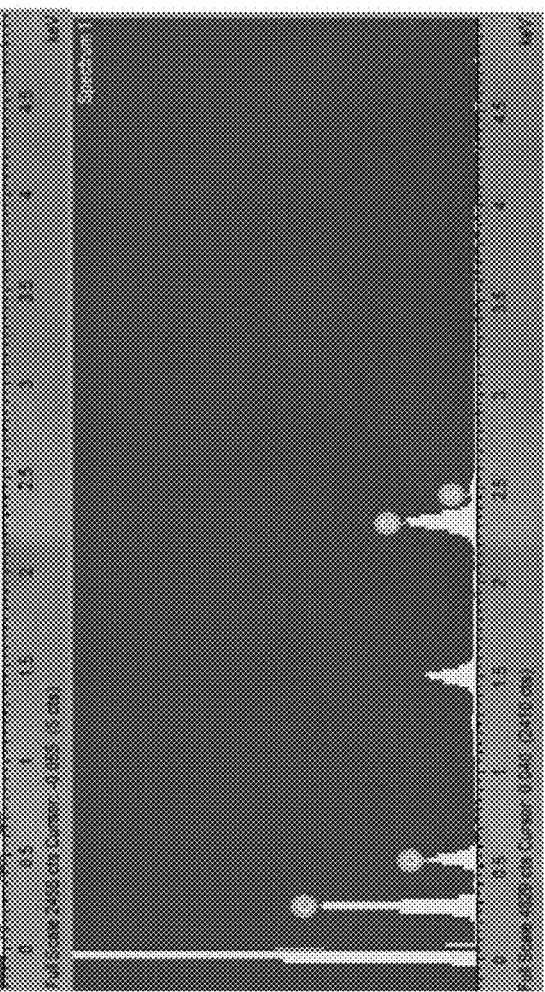
FIG. 5A
FIG. 5B

METHOD FOR REMOVING DYE COMPOUNDS FROM AN AQUEOUS SAMPLE USING A FUNCTIONALIZED ASPHALTENE

BACKGROUND OF THE INVENTION

Technical Field

The present invention is directed to modified asphaltenes. The present invention includes a process for reacting crude asphaltene with acid to form an acid-functionalized asphaltene. The acid-functionalized asphaltene has excellent adsorption properties and can be used for removal of dye compounds from aqueous samples.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Heavy petroleum residue constitutes about 70% of drilled crude oils. A fairly low percent of these residues is being utilized without much processing. Asphaltenes are a class of molecular substances or components found in crude oil, along with resins, aromatic hydrocarbons and saturates such as alkanes. Although found in insignificant quantities, asphaltenes are nonetheless one of the most notable components present in petroleum due to their precipitation and flocculation properties, which often pose a great challenge towards cracking and refining of crude oil. The tendency of asphaltenes to precipitate during crude oil recovery can cause severe consequences such as a sharp decline in oil flow or even blockage of pipelines and processing equipment. Asphaltenes can also increase the viscosity of oil, which can in turn reduce, or even halt, its flow. Furthermore, asphaltenes are known to be coke precursors in acid catalysis and can act as catalyst inhibitors by catalyst deactivation and catalyst poisoning. As such, asphaltenes pose a serious problem to a variety of processes in the petroleum industry.

It has also been reported that asphaltenes are large molecules and are composed of highly condensed polyaromatic rings bearing long aliphatic and alicyclic peripheral substituents along with metals and heteroatoms as part of a ring system. Asphaltenes are primarily composed of the elements hydrogen and carbon, with one to three sulfur, oxygen, or nitrogen atoms per molecule. The basic structure is composed of rings, mainly aromatics, with three to ten or more rings per molecule that are usually fused together to form the polycyclic core of the molecule. [Hasan, M.; Siddiqui, M. N.; and Arab, M., Fuel, Volume 67, No. 8, August, 1988, p. 1131; Shirokoff, J. W.; Siddiqui, M. N.; and Ali, M. F., Energy & Fuels, Volume 11, 1997, p. 561—each incorporated herein by reference in its entirety].

Contamination from dyes has attracted tremendous attention owing to their negative effects on the environment. These toxic pollutants are nonbiodegradable and can accumulate in the human body causing a variety of diseases and disorders. Dyes such as bromophenol blue and methyl orange, widely used in textile and tannery, can cause anemia, insomnia, renal damages, central nervous system damage and dysfunction of the immune system [G. CamCo-Unal, N. L. B. Pohl, Quantitative Determination of Heavy Metal Contaminant Complexation by the Carbohydrate Polymer Chitin, J. Chem. Eng. Data. 55 (2010) 1117-1121; R. Kiefer, W. H. Höll, Sorption of Heavy Metals onto Selective Ion-Exchange adsorbents with Aminophosphonate Functional Groups, Ind. Eng. Chem. 40 (2001) 4570-4576; G. Güçlü, G. Gürdağ, S. Özgümüş, Competitive removal of heavy metal ions by cellulose graft Copolymers, J. Appl. Polym. SCo. 90 (2003) 2034-2039—each incorporated herein by reference in its entirety]. A variety of techniques like adsorption, precipitation, dialysis, ion exchange, reverse osmosis and extraction, have been reported for the removal of dyes contaminants. One of the most attractive among these techniques is presumably the adsorption process due to the availability of different types of efficient adsorbents [K. KesenCo, R. Say, A. Denizli, Removal of heavy metal ions from water by using poly(ethyleneglyCol dimethacrylate-Co-acrylamide) beads, Eur. Polym. J. 38 (2002) 1443-1448; K. E. Geckeler, Polymer-metal Complexes for environmental protection. Chemoremediation in the aqueous homogeneous phase, Pure. Appl. Chem. 73 (2001) 129-136; W. U. Hong, Y. J. In, M. L. Uo, B. I. Shuping, A Simple and Sensitive Flow-Injection On-line PreConcentration Coupled with Hydride Generation Atomic Fluorescence Spectrometry for the Determination of Ultra-trace Lead in Water, Wine, and Rice, Anal. Chem. 23 (2007) 1109-1112; S. J. Shahtaheri, M. Khadem, F. Golbabaei, A. Rahimi-Froushan, M. R. Ganjali, P. Norouzi, Solid phase extraction for evaluation of occupational exposure to Pb (II) using XAD-4 sorbent prior to atomic absorption spectrosCopy, Int. J. Occup. Saf. Ergo. 13(2007) 137-145—each incorporated herein by reference in its entirety]. Inorganic/organic polymer hybrid adsorbents have been widely investigated, and their efficiency of dyes removal has been attributed to the formation of a stronger chemical bonding between dye and adsorbent, for instance, amine motifs in the hybrid materials [Q. Zhang, B. Pan, W. Zhang, B. Pan, Q. Zhang, Arsenate Removal from Aqueous Media by Nanosized Hydrated Ferric Oxide (HFO)-Loaded Polymeric Sorbents: Effect of HFO Loadings, Ind. Eng. Chem. Res. 47 (2008) 3957-3962; G. P. Kumar, P. A. Kumar, S. Chakraborty, M. Ray, Uptake and desorption of Copper ion using functionalized polymer Coated silica gel in aqueous environment, Sep. Purif. Technol. 57 (2007) 47-56; M. Laatikainen, K. Sirola, E. Paatero, Binding of transition metals by soluble and silica-bound branched poly(ethyleneimine). Part 1. Competitive binding equilibria, Colloid Surface A. 296 (2007) 191-205; Y. Tao, L. Ye, J. Pan, Y. Wang, B. Tang, Removal of Pb(II) from aqueous solution on chitosan/$TiO_2$ hybrid film., J. Hazard. Mater. 161 (2009) 718-22; Z.-Y. He, H.-L. Nie, C. Branford-White, L.-M. Zhu, Y.-T. Zhou, Y. Zheng, Removal of MO from aqueous solution by adsorption onto a novel activated nylon-based membrane, Bioresour. Technol. 99 (2008) 7954-8—each incorporated herein by reference in its entirety].

Research on the chemical reactivity of asphaltene has adopted a two-pronged approach. On one hand, attempts are being made to increase or decrease the solubility of asphaltene so as to mitigate the flocculation properties of asphaltene and its impact on crude oil viscosity or to increase precipitation of asphaltene and thereby its separation from crude oil, respectively. On the other hand, there are ongoing efforts in turning asphaltene into a useful material in industries such as but not limited to polymer and environmental protection.

The present disclosure provides a process for chemically modifying asphaltene to produce a functionalized asphaltene with physical properties that are suitable for applications such as but not limited to removal of pollutant compounds from water by adsorption.

BRIEF SUMMARY OF THE INVENTION

According to a first aspect, the present disclosure provides a functionalized asphaltene comprising 10-35% by weight of elemental oxygen per total weight of the functionalized asphaltene, 3-10% by weight of elemental nitrogen per total weight of the functionalized asphaltene and 3-10% by weight of elemental sulfur per total weight of the functionalized asphaltene. The functionalized asphaltene is obtained by refluxing a petroleum asphaltene with 70% concentrated nitric acid, and has at least one active group selected from the group consisting of an amine group, a nitro group, a carbonyl group, a carboxylic group and a hydroxyl group covalently bonded to an asphaltene core.

In certain embodiments, the functionalized asphaltene has an average particle size of 10-20 nm.

In certain embodiments, the functionalized asphaltene has a particle size distribution of 0.5-100 nm wherein at least 60% of the particles have a particle size of 10-20 nm.

In some embodiments, the functionalized asphaltene has a specific surface area of no higher than 10 $m^2/g$.

In some embodiments, the functionalized asphaltene has an adsorption average pore width of 4-10 nm.

According to a second aspect, the present disclosure provides a process for preparing the functionalized asphaltene. The process comprises refluxing an asphaltene-acid suspension at 70-90° C. for 1-2 h to form the functionalized asphaltene. The asphaltene-acid solution comprises the petroleum asphaltene and the acid.

In certain embodiments, the acid is a 70% v/v nitric acid.

In certain embodiments, during the refluxing, the asphaltene-acid solution is agitated at 200-500 rpm.

In certain embodiments, the asphaltene-acid solution has a concentration of 0.025-0.05 g of the petroleum asphaltene per ml of the acid solution.

In one embodiment, the preparation process further comprises dispersing the petroleum asphaltene in the acid solution.

In one embodiment, the preparation process further comprises cooling the asphaltene-acid solution after the refluxing, separating and purifying the functionalized asphaltene, and drying the functionalized asphaltene.

In one embodiment, the preparation process further comprises pulverizing the functionalized asphaltene.

According to a third aspect, the present disclosure provides a method for removing a dye compound from an aqueous sample with the functionalized asphaltene. In the method, the aqueous sample is contacted with the functionalized asphaltene of claim 1 to adsorb the dye compound onto the functionalized asphaltene.

In some embodiments, the functionalized asphaltene has an adsorption capacity of 1-5 mg of the dye compound per g of the functionalized asphaltene.

In one embodiment, the aqueous sample is contacted with functionalized asphaltene for 2-7 h.

In another embodiment, the aqueous sample is contacted with 1-10 mg/ml of functionalized asphaltene.

In certain embodiments, the dye compound is bromophenol blue and the aqueous sample is contacted with the functionalized asphaltene at pH 4-9.

In alternative embodiments, the dye compound is methyl orange and the aqueous sample is contacted with the functionalized asphaltene at pH of 2.5-4 or 8-9.5.

In one embodiment, the method further comprises desorbing the bromophenol blue from the functionalized asphaltene at a pH of lower than 4 and higher than 9.

In another embodiment, the method further comprises desorbing the methyl orange from the functionalized asphaltene at a pH of higher than 4 and lower than 8.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 1A is an IR spectrum of virgin Arab Heavy asphaltene.

FIG. 1B is an IR spectrum of Arab Heavy asphaltene after functionalization, clearing showing the presence of C=O groups.

FIG. 3A is an SEM image of functionalized Arab Heavy asphaltene at 20.0× magnification.

FIG. 3B is an SEM image of functionalized Arab Heavy asphaltene at 15.0× magnification.

FIG. 5A is an EDX spectrum of virgin Arab Heavy asphaltene.

FIG. 5B is an EDX spectrum of functionalized virgin Arab Heavy asphaltene, showing a higher oxygen content.

DETAILED DESCRIPTION OF THE EMBODIMENTS

Figures 2A, 2B:
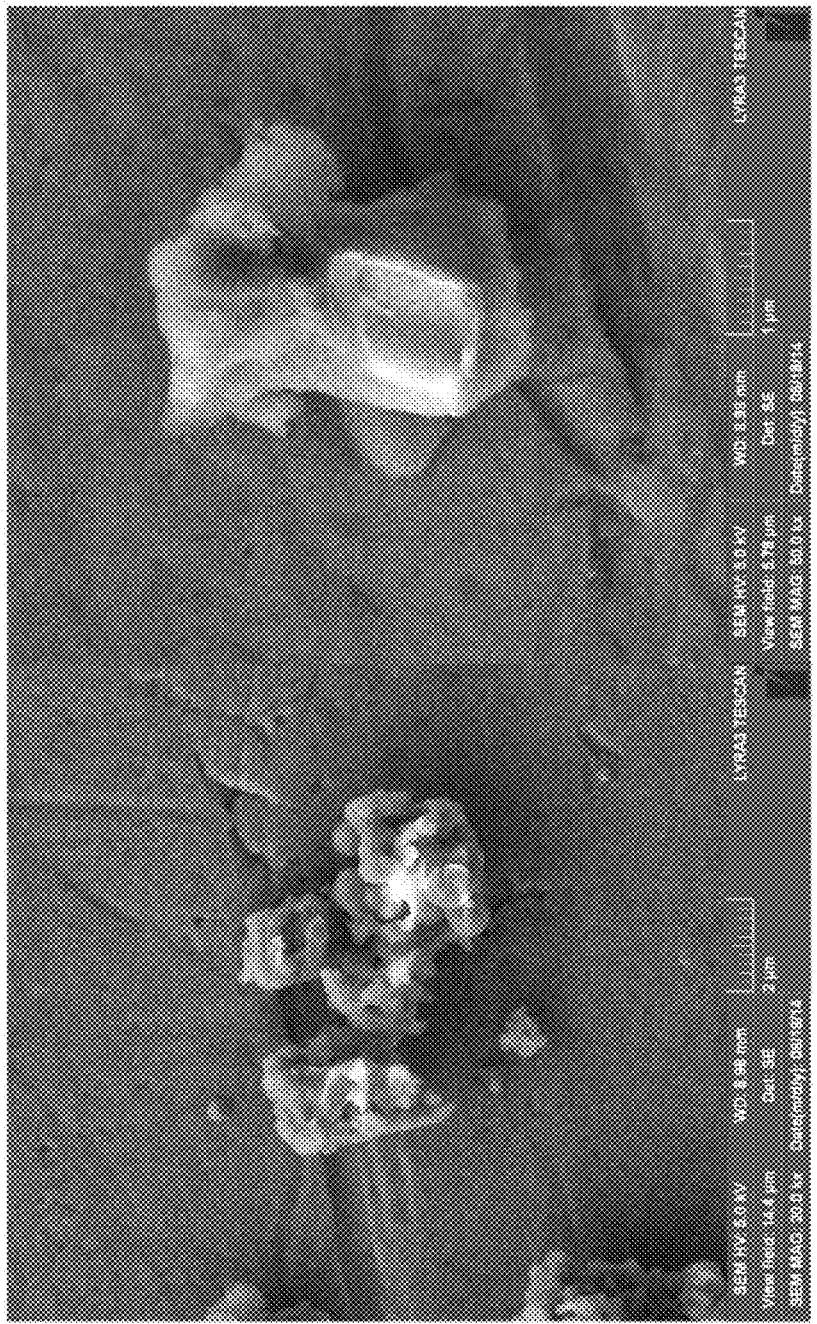
FIG. 2A is an SEM image of virgin Arab Heavy asphaltene at 20.0× magnification.
FIG. 2B is an SEM image of virgin Arab Heavy asphaltene at 50.0× magnification.
Figures 2C, 2D:
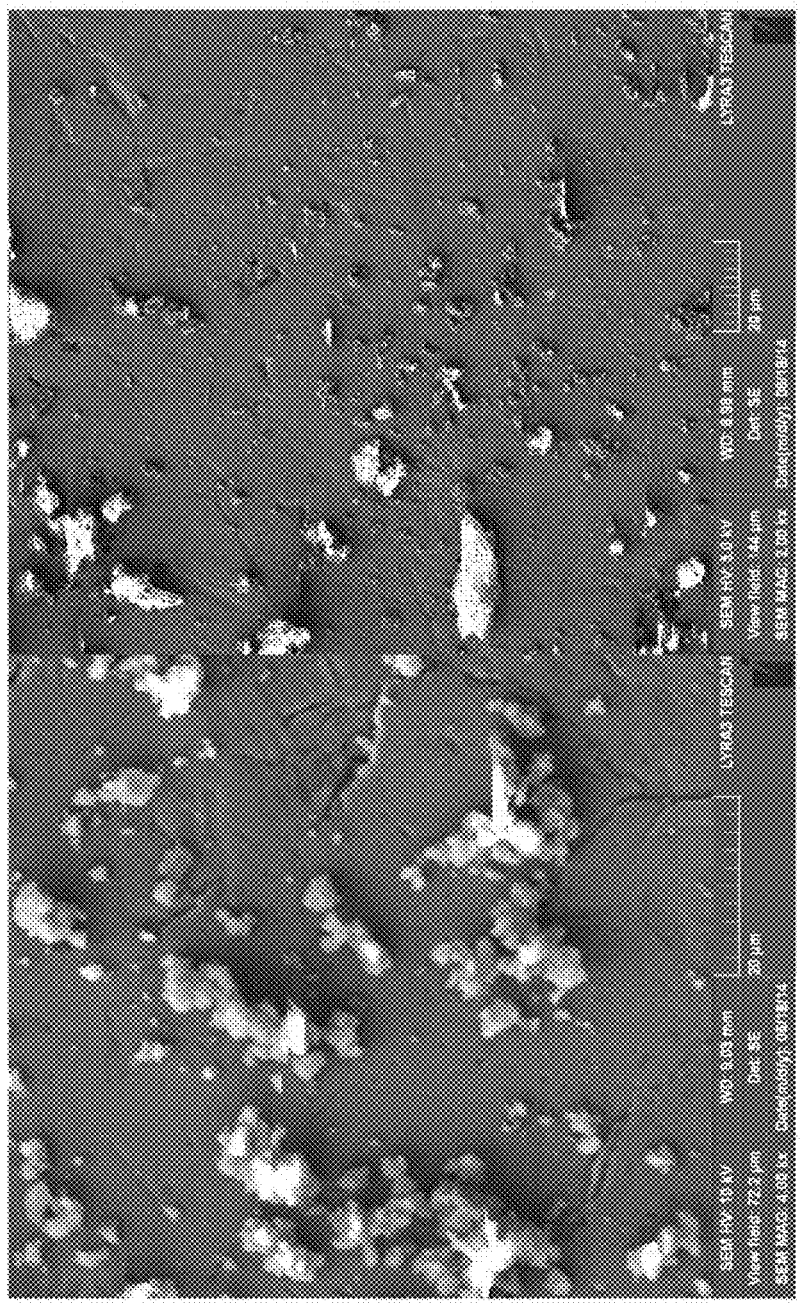
FIG. 2C is an SEM image of virgin Arab Heavy asphaltene at 2.00× magnification.
FIG. 2D is an SEM image of virgin Arab Heavy asphaltene at 4.00× magnification.
Figures 3C, 3D:
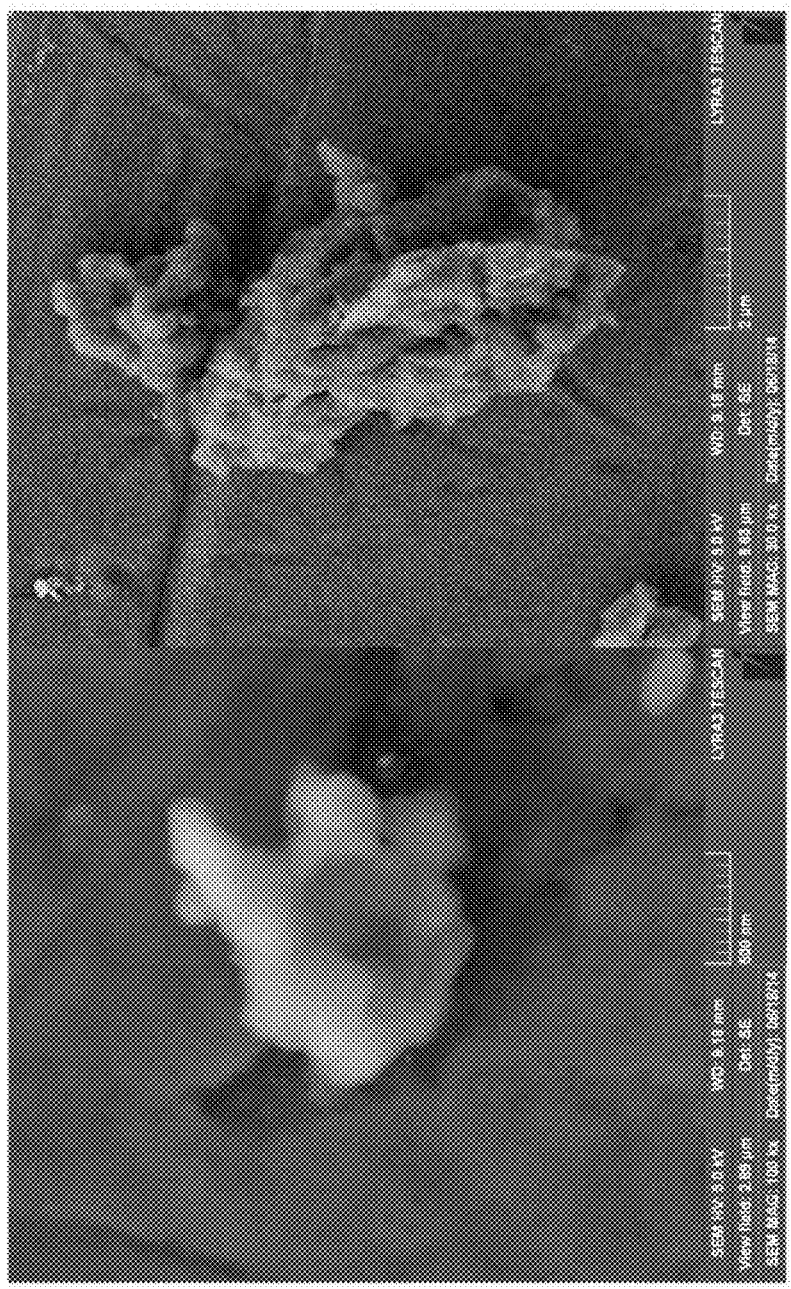
FIG. 3C is an SEM image of functionalized Arab Heavy asphaltene at 100× magnification.
FIG. 3D is an SEM image of functionalized Arab Heavy asphaltene at 30.0× magnification.

Referring now to the drawings, wherein like reference numerals designate identical or corresponding parts throughout the several views.

In the present disclosure, a process for modifying asphaltene where a crude asphaltene derived from crude oil (e.g., a petroleum asphaltene) is reacted with acid is provided. The reaction with the acid at least partially oxidizes and/or nitrates the asphaltene and imparts functional groups including any of amine, nitro, carbonyl, carboxylate and hydroxyl onto the surface of the modified asphaltene product, thereby producing a functionalized asphaltene.

As used herein, the terms "functionalization" or "surface functionalization" refer to a chemical process that introduces chemical functional groups to a surface of a material, which in the case of the present disclosure, is asphaltene.

As used herein, "asphaltene" refers to a class of large molecules that are found in crude oil that are composed of multiple or polyaromatic rings bearing long aliphatic and alicyclic substituents along with trace amounts of metals such as vanadium and nickel and trace amounts of heteroatoms such as sulfur, oxygen and nitrogen as part of a ring system. Structurally, there are usually 3-10 rings per large asphaltene molecule, mostly aromatics but not excluding naphtenes and other non-aromatic cyclic rings, that are fused together to form the polycyclic core of the molecule. [Hasan, M.; Siddiqui, M. N.; and Arab, M., Fuel, Volume 67, No. 8, August, 1988, p. 1131; Shirokoff, J. W.; Siddiqui, M. N.; and Ali, M. F., Energy & Fuels, Volume 11, 1997, p. 561—each incorporated herein by reference in its entirety]. Asphaltenes are insoluble in light paraffins such as n-pentane or n-heptane, but soluble in aromatic solvents such as toluene.

The asphaltene subjected to the functionalization process of the present disclosure, derived from Arab heavy crude, preferably has an American Petroleum Institute (API) gravity of 25.0-30.0. One formula to calculate API gravity is from a known specific gravity value of a hydrocarbon:

$$API \text{ gravity} = \frac{141.5}{SG} - 131.5 \qquad \text{Eq. (A)}$$

The asphaltene modification or functionalization process of the present disclosure includes a step of dispersing crude asphaltene in an acid mixture solution by agitation, preferably by sonication, more preferably sonication at ultrasonic frequencies of >20 kHz for 1-2 h to form a homogeneous asphaltene-acid suspension having a concentration of 0.025-0.05 g of crude asphaltene per ml of the 70% concentrated nitric acid. The asphaltene-acid suspension is then refluxed with simultaneous agitation at 200-500 rpm, preferably 250-350 rpm for 1-2 h, at 70-90° C. After the acid reflux treatment, the asphaltene-acid mixture is cooled to room temperature then the functionalized asphaltene is purified and extracted by repeated cycles of dilution with distilled and deionized water, centrifugation and decanting of the supernatant until washings color changes from pale yellow to colorless. The functionalized asphaltene is dried overnight at a temperature of 65-110° C., preferably 70-90° C. which afforded 70-75% yield by weight. It is not required to subject the functionalized asphaltene to other forms of thermal treatment, such as calcination and sintering, that further physically and/or chemically modifies the asphaltene (e.g. phase transformation, densification).

The functionalized asphaltene is then loaded into a planetary ball mill and crushed to fine powdered form and used as it is.

In certain embodiments, the functionalization process is preceded by a process for extracting crude asphaltene from crude oil. The crude oil is initially mixed with an alkane solvent (n-heptane) to form a resid solution. The resid solution is heated for 1-3 h, preferably 90-100° C., then cooled overnight at room temperature, during which the asphaltene contained in the crude oil will precipitate (as asphaltene is insoluble in light paraffin solvents). The precipitated crude asphaltene is separated from the crude oil by filtration then purified from the filtrate using toluene (in which asphaltene is soluble). After toluene is removed from the extracted asphaltene, the asphaltene is washed multiple times with an alkane solvent to remove maltenes, then dried. The recovered asphaltenes were dried in an oven for about 2 h at 105° C. to obtain a constant weight.

The functionalized asphaltene prepared as described herein has an average particle or diameter size of 5-50 nm, preferably 10-40 nm, and a particle size distribution of 0.5-200 nm, where at least 60% of particles fall within the average particle size range, preferably 60-70%.

In terms of elemental composition, the changes brought by the functionalization process include an increase in nitrogen and/or oxygen contents, preferably both, which are attributed to nitration and oxidation reactions that take place during the functionalization. As revealed by energy dispersive X-ray analysis, the functionalized asphaltene has a nitrogen content of 3-10% by weight, and 3-10% by weight of elemental sulphur per total weight of the functionalized asphaltene.

As revealed by Fourier transform infrared (FT-IR) analysis, the functionalized asphaltene, as a result of nitration and oxidation by concentrated nitric acid, contains at least type of group such as amine, nitro, carboxyl, carbonyl and hydroxyl functional groups, preferably all such groups. The major peaks of FT-IR spectrum of the functionalized asphaltene, which are lacking in the FT-IR spectrum of the unmodified (virgin) asphaltene, include 3200-3650 $cm^{-1}$ for O—H and N—H groups, preferably 3350-3600 $cm^{-1}$, more preferably 3400-3550 $cm^{-1}$ (i.e. up to 88.5% absorbance), 1700-1760 $cm^{-1}$ for C=O and COOH groups, preferably 1715-1745 $cm^{-1}$ (i.e. up to 86.5% absorbance, 1500-1550 $cm^{-1}$ for N—O groups, preferably 1525-1540 $cm^{-1}$, (i.e. up to 88.0% absorbance) and 1300-1350 $cm^{-1}$, (up to 90% absorbance, for N—O and C—N groups. Apart from the prevalence of these major peaks in the FT-IR spectrum of the functionalized asphaltene that correspond to amino, nitro, carbonyl, carboxylic and hydroxyl groups, the functionalization process also appears to slightly reduce C—H groups (i.e. peaks at 2800-2950 $cm^{-1}$, preferably 2850-2930 $cm^{-1}$) from a peak intensity of 80-90% absorbance to 90-98% absorbance., Another peak at 1000-1050 $cm^{-1}$, preferably 1025-1045 $cm^{-1}$, that corresponds with aliphatic amines, alcohols, carboxylic acids, esters and ethers is present in the FT-IR spectra of both the functionalized asphaltene and the unmodified asphaltene, with little change to the intensity of the peak.

Scanning electron micrographs of the functionalized asphaltene show that the unmodified (virgin) asphaltene particle has a flat and smooth surface having a root-meansquare roughness value ($R_q$) of lower than 0.5 nm. Compared to its unmodified counterpart, the functionalized asphaltene exhibits an abrasive surface morphology, where the $R_q$ is 0.5-50 nm, more preferably 5-20 nm. The root-mean-square roughness value ($R_q$) can be calculated according to Eq. (B):

$$R_q = \sqrt{\frac{1}{n}\sum_{i=1}^{n} y_i^2} \qquad \text{Eq. (B)}$$

where n is number of sample measurements and $Y_i$ is the sum of absolute values of surface profile coordinates.

In addition, the functionalized asphaltene particle is dendrimer-like, having ultrafine, nanotube protrusions emanating from the particle core at a density of 0.5-5 protrusions/$nm^2$, preferably 2-3.5 protrusions/$nm^2$. These nanotube protrusions have a diameter or width of 0.01-0.25 nm, preferably 0.02-0.1 nm. All of these observations of the surface morphology of the functionalized asphaltene, along with the FT-IR, EDX, DSC and TGA characterization results, agree well with the inference that functional groups are covalently bound to the asphaltene core or attached to a surface thereof, thereby coating the surface of a functionalized asphaltene particle. On the molecular level, the amine, nitro, carboxyl, carbonyl and hydroxyl functional groups are peripheries attached to the polycyclic core of the asphaltene molecule, along with the aliphatic and alicyclic peripheral substituents.

The functionalized asphaltene has a Brunauer-Emmett-Teller (BET) specific surface area of no higher than 10 $m^2/g$, preferably 3-6 $m^2/g$. The functionalized asphaltene is also nanoporous, having an adsorption average pore width of the functionalized asphaltene is 1-10 nm (10-100 Å), preferably 5-7 nm (50-70 Å).

As indicated by differential scanning calorimetry (DSC), the functionalization process increases the combustibility of the asphaltene. As used herein, "combustibility" refers to a measure of how easily (i.e. at what temperature) an asphaltene sample, which is a fuel, will react with oxygen to produce a high-temperature exothermic redox chemical reaction. The higher combustibility of the functionalized asphaltene is attributed to the presence of organic functional groups coating the surface of the functionalized asphaltene particle. The combustion of the functionalized asphaltene, which is an exothermic process, can take place at temperatures that are equal or lower than 300° C., preferably 100-280° C. The DSC curve of the functionalized asphaltene, where the heat flow rate is expressed as a function of temperature, exhibits a prominent and broad peak at 300-600° C., compared to a small peak at 400-500° C. of the virgin and unmodified asphaltene.

Consistent with the increase in combustibility of the functionalized asphaltene as shown by DSC measurements, thermogravimetric analyses indicate that the functionalization process has reduced the thermal stability of the asphaltene. While the virgin asphaltene decomposes or suffers from weight loss in a single peak at 400-500° C., the weight losses for the functionalized asphaltene take place in multiple steps. In one embodiment, the first step with gradual weight loss occurs from around 150° C. to around 300° C., more preferably 200-275° C. while the second minor decomposition takes places in around 300-400° C., preferably 300-325° C.

Another embodiment of the present disclosure relates to a method for removing one or more of a dye compound and a heavy metal ion from an aqueous sample by adsorption with the functionalized asphaltene. Examples of dye compounds that the functionalized asphaltene is capable of adsorbing include but are not limited to methyl violet, malachite green, thymol blue, methyl yellow, methyl orange, bromophenol blue, Congo red, methyl purple, bromocresol green, azolitmin, phenol red, methyl red, bromocresol purple, bromothymol blue, neutral red, indigo carmine, naptholphthalein, cresolphthalein, thymolphthalein, cresol red and Alizarine yellow R. In one embodiment, the functionalized asphaltene is capable of adsorbing bromophenol blue and methyl orange.

To remove the one or more dye compounds from an aqueous sample, the aqueous sample is contacted with the functionalized asphaltene, in batch mode, for 2-7 h, When the removal is executed in batch mode, the aqueous sample contains 1-10 mg of the functionalized asphaltene per ml of the aqueous sample, preferably 8-10 mg.

Specifically for bromophenol blue and methyl orange, the functionalized asphaltene has an adsorption capacity of 1-5 mg of the adsorbate per g of the adsorbent, preferably 1.5-3.0 mg/g.

The adsorption of bromophenol blue and methyl orange by the functionalized asphaltene fits well with at least one of Langmuir, Freundlich and Temkin isotherm models, thereby inferring that the adsorption occurs as a monolayer and as a heterogeneous surface adsorption.

For the Langmuir isotherm model, separation factor or equilibrium parameter (&) can be used to describe the favorability of adsorption on the polymer surface. A favorable adsorption is indicated when the $R_L$ value is between $0<R_L<1$, whereas the $R_L$ values outside the range describes an unfavorable adsorption. For the adsorption of bromophenol blue and methyl orange, the functionalized asphaltene exhibits a Langmuir separation factor or equilibrium parameter, $R_L$, of 0.15-0.8 for an initial adsorbent concentration spanning 10-75 $mg/dm^3$. In one embodiment, the $R_L$ values for bromophenol blue and methyl orange are 0.3-0.76 mg/g and 0.16-0.59 mg/g, respectively.

The adsorption of bromophenol blue and methyl orange by the functionalized asphaltene is also pH-sensitive. The functionalized asphaltene is contacted to adsorb bromophenol blue from an aqueous sample when the aqueous sample has a pH of 6-7. The adsorption of methyl orange by the functionalized asphaltene takes place at pH of 2.5-4. This means that the adsorbed bromophenol blue and methyl orange can be easily desorbed from the functionalized asphaltene to regenerate the adsorbent at a pH of lower than 4 and higher than 9 for bromophenol blue and a pH of higher than 4 and lower than 8 for methyl orange by treating the asphaltene onto which a dye has been adsorbed with base or acid such that the pH conditions encourage release of the adsorbed dye from the adsorbent.

In thermodynamics, the Gibbs free energy (ΔG) is used to describe the spontaneity of a process, and is defined by Gibbs equation:

$$\Delta G = \Delta H - T\Delta S \qquad \text{Eq. (B)}$$

where ΔH is the enthalpy change, ΔS is the entropy change, T the absolute temperature and ΔG the Gibbs free energy of the system. A summary of spontaneity based on the relationship among ΔH, ΔS and ΔG in accordance with the Gibbs free energy thermodynamic system is given in Table B.

TABLE B

Summary of Gibbs free energy thermodynamic system.

| ΔH | ΔS | ΔG | Spontaneity |
|---|---|---|---|
| Positive | Positive | May be positive or negative, depending on T | Yes, if T is high enough |
| Negative | Positive | Always negative | Always spontaneous |
| Negative | Negative | May be positive or negative, depending on T | Yes, if T is low enough |
| Negative | Negative | Always positive | Never spontaneous |

The adsorption of bromophenol blue and methyl orange by the functionalized asphaltene is also temperature-dependent, and is carried at 20-60° C., preferably 35-55° C. These adsorption events are also spontaneous and endothermic, as evidenced by negative ΔG values (Gibbs free energy) ranging −5 kJ/mol to −20 kJ/mol and positive ΔH values (enthalpy of reaction) ranging +5 kJ/mol to +20 kJ/mol in a temperature range of 295-330 K. An increase in the adsorption temperature leads to an increase in randomness or disorder in the system, as revealed by positive ΔS values (entropy) ranging +5 kJ/mol to +20 kJ/mol in a temperature range of 295-330 K.

The following examples outline various protocols including protocols for separating asphaltene from crude oil residue, functionalizing the extracted asphaltene with an acid, characterizing the functionalized asphaltene, removing dye compounds from an aqueous sample by adsorption with the functionalized asphaltene, and evaluating adsorption properties of the functionalized adsorbent based on various measured or calculated adsorption parameters.

In these examples, an adsorbent from the functionalization of asphaltenes was prepared in excellent yield from inexpensive starting materials. The adsorbent was found to have an excellent adsorption capacity for BPB and MO ions. The adsorption followed Langmuir, Freundlich and Temkin isotherm models as well as Lagergren pseudo second-order kinetic model. The negative ΔG values and positive ΔH values ensured the spontaneity and the endothermic nature of the adsorption process. The excellent adsorption and desorption efficiencies implied the efficacy of the adsorbent in removing as well as recovering the metal ions from aqueous solution. The effective recycling of the adsorbent and its reuse would enable it to be used in the treatment of contaminated water in industry.

It is to be understood that the following examples have been included for strictly illustrative purposes, and are not intended to limit the scope of the present disclosure.

EXAMPLE 1

Separation of Asphaltene from Crude Oil

First, 7.0 g of Arab Heavy residue or crude oil was transferred to the 200 ml beaker and heated with a very small amount of n-heptane in order to homogenize the solution. This resid solution, after mixing well to become homogeneous, was carefully transferred to a 2 L flask and 700 ml of n-heptane was added to the same flask. The flask containing the resid solution was fitted with a mechanical stirrer and placed on the water bath. The resid solution was heated at 90° C. on the steam bath with continuous stirring for about 2 hours in order to maximize the solubility of the resid in n-heptane. After two hours of mixing, the resid solution covered with aluminum foil was left on the working bench to cool at room temperature for about 24 hours. The long cooling time produces efficient precipitation of asphaltenes. The resid solution was filtered using a Millipore filtration apparatus with 0.8 μm (37 mm) pore size filter paper. All insoluble material was soxhlet extracted with toluene and filtered again using same filtering apparatus. The insoluble material was removed as sludge (coke) and the soluble material, asphaltene, was recovered after evaporating toluene completely. The asphaltene was collected in a 250 ml beaker and washed several times with small portions of n-heptane, in order to remove any traces of maltenes, until washings became colorless. The recovered asphaltenes were dried in an oven for about 2 hours at 105° C. to obtain a constant weight. The filtrate, maltene, was recovered by evaporating the n-heptane on the steam bath using a rotavapor with continuous blowing of dry nitrogen until a constant weight of the maltene was obtained.

EXAMPLE 2

Functionalization of Asphaltene 10 g of the asphaltene separated from the Arab Heavy crude oil residue was dispersed for 1 hour by sonication in a 70% v/v concentrated nitric acid solution. The asphaltene-acid mixture was refluxed while stirring vigorously for 1-2 hours at 70-90 C temperature. After the refluxing, the asphaltene-acid mixture was allowed to cool at room temperature. The functionalized asphaltene was purified by repeated cycles of dilution with distilled water, centrifugation and decanting the solutions until the pH was approximately 5, in order to extract the residual acids. After the purification step, the functionalized asphaltene was dried overnight in an oven at 100° C. and was pulverized in a ball-mill.

EXAMPLE 3

Characterization of the Functionalized Asphaltene—Fourier Transform Infrared Spectroscopy The virgin Arab Heavy asphaltene and the functionalized asphaltene prepared thereof were characterized by Fourier transform infrared spectroscopy (FT-IR) for an analysis of the organic functional groups present in the samples, and the IR spectra of the virgin and functionalized asphaltene samples are given in FIGS. 1A and 1B, respectively.

The peaks in the IR spectra were identified based on characteristic IR absorption frequencies. Based on the analysis and compared to its virgin version, the functionalized asphaltene shows a strong presence of C═O groups and also possibly C—N groups. C═O groups are associated with carboxylic acids, but also possibly esters, aldehdyes and ketones. The increased intensity of the peak at 3454.4 $cm^{-1}$ may be attributed to an increase in O—H groups as induced by acid oxidation and also newly formed N—H or amine groups in the functionalized asphaltene. The formation of amine groups in the functionalized asphaltene is further supported by the peak at 1342.1 $cm^{-1}$ which corresponds to C—N groups in aromatic amines. The C═C aromatic groups in the 1400-1600 $cm^{-1}$ absorption wavelength region do not appear to differ significantly between the virgin asphaltene and the functionalized asphaltene, whereas C—H groups in the 2850-3000 $cm^{-1}$ absorption wavelength region appear to have reduced in amount in the functionalized asphaltene.

EXAMPLE 4

Characterization of the Functionalized Asphaltene—Scanning Electron Microscopy Scanning electron microscopy (SEM) images taken of the Arab Heavy asphaltene before (FIGS. 2A-2D) and after (FIGS. 3A-3D) the acid functionalization process show that the morphologies of the two samples are different. The functionalized asphaltene has a relatively rougher and more porous surface, which is attributed to the presence of functional groups including but not limited to amine, nitro, carboxyl, carbonyl and hydroxyl groups bound to and therefore coating the surface of the functionalized asphaltene.

EXAMPLE 6

Characterization of the Functionalized Asphaltene—Differential Scanning Calorimetry Differential scanning calorimetry or DSC is a thermoanalytical technique in which the difference in the amount of heat required to increase the temperature of a sample and an inert reference material is measured as a function of temperature. In the present disclosure, the DSC measurements are carried out in the presence of oxygen or air so that the oxidative stability of the virgin Arab Heavy asphaltene and the functionalized asphaltene can be determined, and the DSC curves are shown in FIG. 4.

Figure 4:
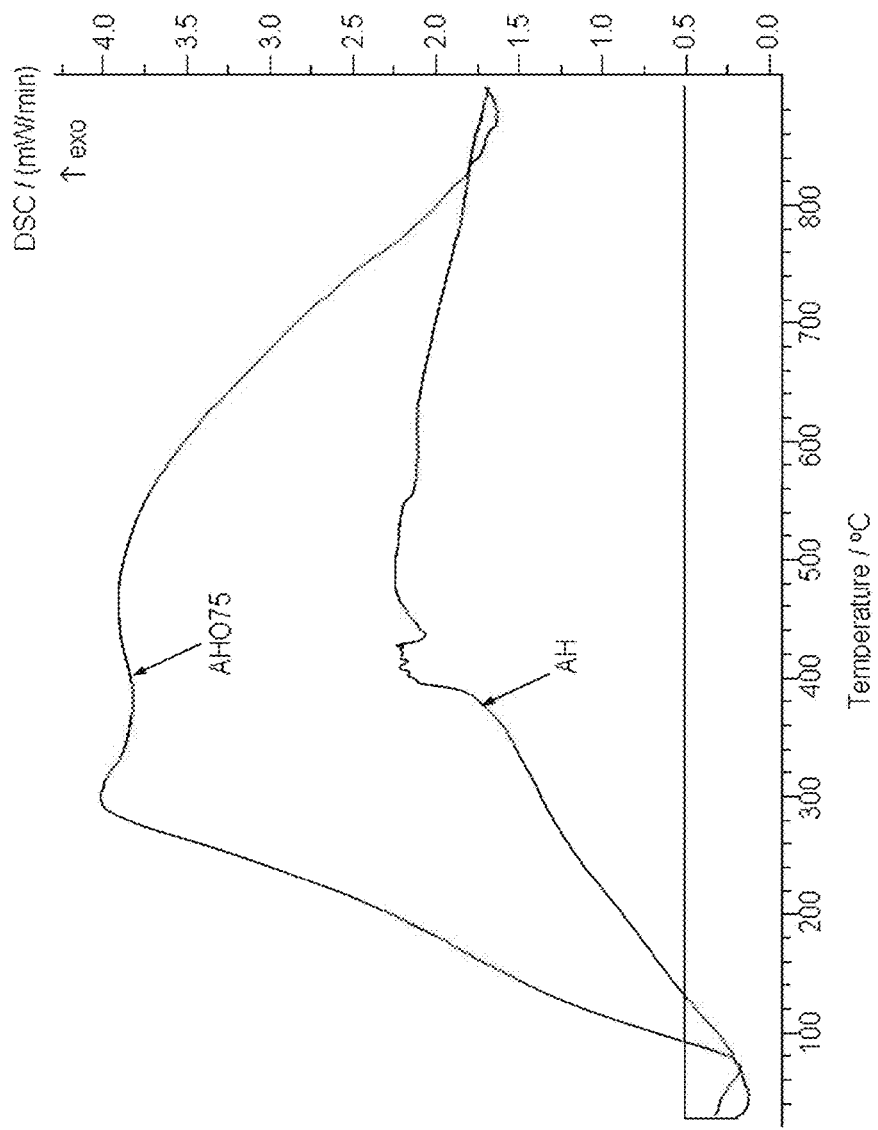
FIG. 4 is a DSC curve of virgin Arab Heavy asphaltene (AH) and functionalized Arab Heavy asphaltene (AH075).

As shown in FIG. 4, the combustion of both the unmodified asphaltene and the functionalized asphaltene is an exothermic process. The DSC curve for the functionalized asphaltene exhibits a sharper and higher peak, thereby indicating greater exothermicity which agrees well with the strong presence of C=O groups and other organic functional groups indicated by the FT-IR spectra. The functionalized asphaltene also begins combustion at a lower temperature compared to the virgin asphaltene, i.e. lower than 300° C.

EXAMPLE 7

Figure 6:
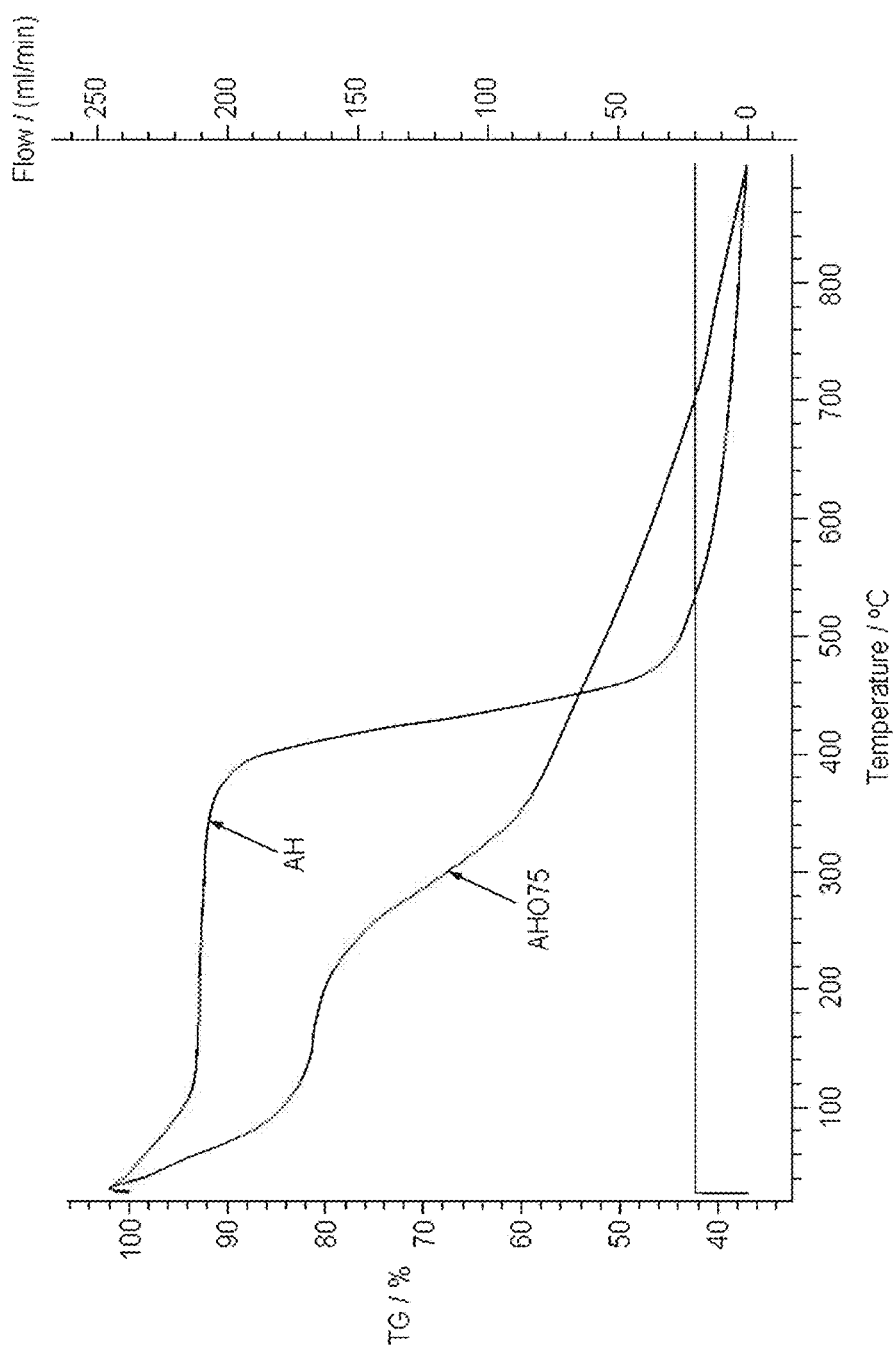
FIG. 6 is a TGA curve of virgin Arab Heavy asphaltene (AH) and functionalized Arab Heavy asphaltene (AH075).

Characterization of the Functionalized Asphaltene—Thermogravimetric Analysis The thermal stability of the virgin Arab Heavy asphaltene and the functionalized asphaltene was determined by thermogravimetric analysis (TGA), and the TGA curves are shown in FIG. 6.

The TGA results, consistent with the DSC results, indicate that the functionalization process has reduced the thermal stability of the asphaltene. While the virgin asphaltene decomposes or suffers from weight loss in a single peak at 400-500° C., the weight losses for the functionalized asphaltene take place at two steps. The first step with gradual weight loss from around 150° C. to around 300° C., while the second minor decomposition takes places in around 300-400° C.

EXAMPLE 8

Characterization of the Functionalized Asphaltene—Brunauer-Emmett-Teller Surface Area Analysis The Brunauer-Emmett-Teller (BET) surface area of the virgin asphaltene and functionalized asphaltene was analysed and the results are summarized in Table 2.

TABLE 2

BET surface area and adsorption average pore width data of asphaltene samples.

| Sample | BET surface area (m²/g) | Adsorption average pore width (Å) |
|---|---|---|
| AH | 5.4144 | 64.4673 |
| AH075 | 3.8268 | 52.8895 |

EXAMPLE 9

Characterization of the Functionalized Asphaltene—Energy-Dispersive X-Ray Spectroscopy The elemental analysis of the virgin and functionalized asphaltene samples was carried using the energy-dispersive X-ray (EDX) technique, and the results thereof are given in FIGS. 5A, 5B and Table 3. The sharp increase in oxygen content in the functionalized asphaltene agrees well with the strong presence of C=O groups and other organic functional groups indicated by the FT-IR spectra. The increase in nitrogen content also agrees with the postulated N—H formation in the functionalized asphaltene in the FT-IR spectra.

TABLE 3

EDX elemental analysis of asphaltene samples.

| Sample | C | H | N | S | O (O = 100% − C—H—S) |
|---|---|---|---|---|---|
| AH | 81.28 | 7.44 | 1.19 | 7.17 | 2.92 |
| AH075 | 57.08 | 4.13 | 5.31 | 5.65 | 27.83 |

EXAMPLE 10

Dye Adsorption by the Functionalized Asphaltene

The functionalized asphaltene was evaluated for its adsorbent properties using the dye compounds bromophenol blue (BPB) and methyl orange (MO). The BPB, MON and all other reagents were procured from BDH Chemicals and were of analytical grade. Deionized water used throughout the adsorption investigations.

The adsorption properties of the functionalized asphaltene for BPB and MO ions were determined by spectrophotometric method. The procedure for dye adsorption was as follows: A mixture of functionalized asphaltene (200 mg) in 25 ml of 25 mg/L dye solution was stirred using a temperature-controlled shaker-bath at different pH values (pH=2, 3, 4, 5, 6 or 7) for 24 h. The adsorbent was filtered and the filtrate is then analyzed by UV-VIS spectrophotometer to find out the amount of dye remained.

The adsorption capacity ($q_{dye}$) can be calculated using Eq. (1):

$$q_{dye} = \frac{(C_i - C_e)V}{W} \text{mg/g} \qquad \text{Eq. (1)}$$

where $C_i$ and $C_e$ are the initial and equilibrium concentrations of the dye, respectively, W is the weight of the adsorbent in g and V is the volume of the solution in milliliter.

Adsorption kinetic studies were carried out by stirring 25 ml of 25 mg/L solution in a preferred pH buffer with adsorbent (200 mg) at different temperatures and the dye concentrations were determined by taking a small amount of filtered aliquots at various time intervals. Adsorption isotherms were constructed by determining the adsorption capacities of the adsorbent at different dye concentrations ranging from 10 mg/L to 100 mg/L at ambient temperature. Thermodynamic parameters ΔG, ΔH and ΔS were calculated using data from experiments carried out at different temperatures.

Figure 7:
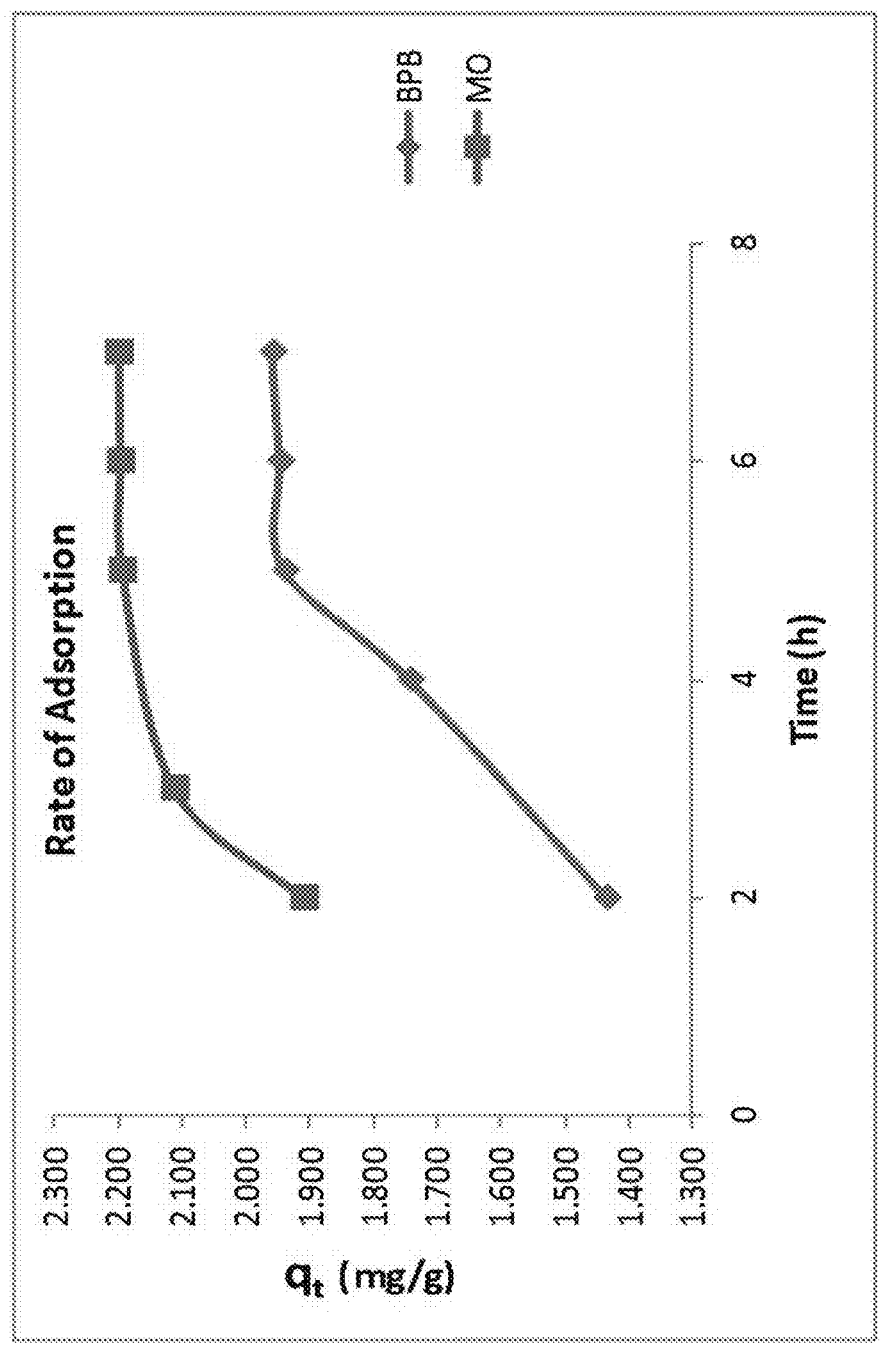
FIG. 7 shows the adsorption kinetic curves of methyl orange (MO) and bromophenol blue (BPB) at 25 ppm in aqueous samples.
Figure 8:
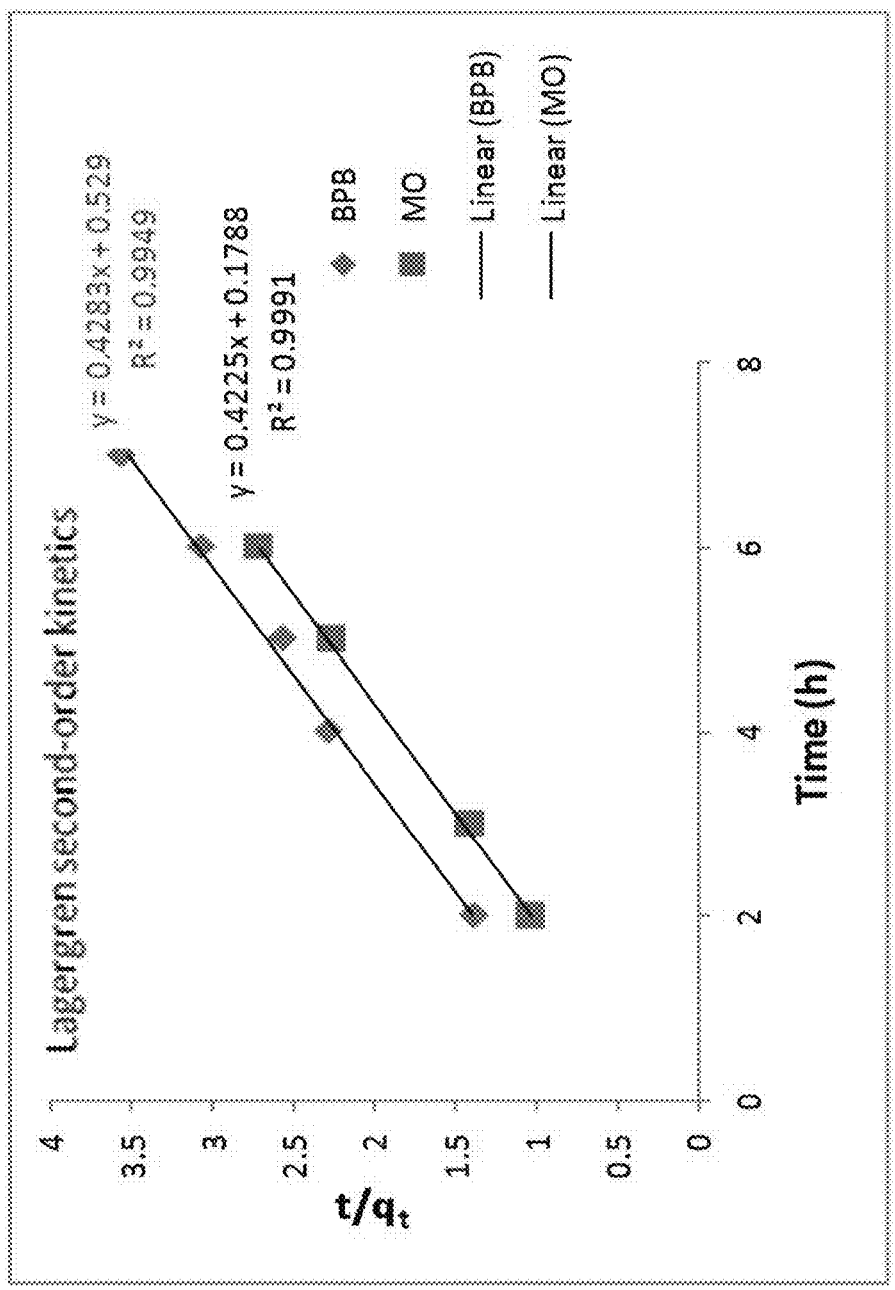
FIG. 8 shows the Lagergren second-order kinetic model adsorption curve of MO and BPB on a functionalized asphaltene adsorbent at 295 K.

A plot of adsorption capacity versus time determines the rate of adsorption in FIG. 7. It was found that the adsorption equilibrium for BPB and MO ions by adsorbent reached in about 1.5 h. Lagergren adsorption kinetic model has been reported as a suitable tool to investigate the adsorption properties. The following Eq. (3) and Eq. (4) express the linear pseudo first and pseudo second-order kinetic equations for the Lagergren model, respectively:

$$\log(q_e - q_t) = \log q_e - \frac{k_1 t}{2.303} \qquad \text{Eq. (2)}$$

$$\frac{t}{q_t} = \frac{1}{k_2 q_e^2} + \frac{t}{q_e} \qquad \text{Eq. (3)}$$

where $k_1$ and $k_2$ are the first-order and second-order rate constant, respectively; $q_t$ and $q_e$ are the adsorption capacities of the metal ions at time t and at equilibrium, respectively. Although BPB and MO both gave regression value ($R^2$) above 0.9 for the pseudo first-order Lagergren kinetic model, there is a vast difference between the experimental adsorption capacity and the calculated adsorption capacity so the graph representing the kinetic model has not been displayed. The MO and BPB were well fitted in the second-order Lagergren kinetic model (FIG. 8) with very close experimental adsorption capacity and the calculated adsorption capacity (Table 4).

TABLE 4

Lagergren pseudo second-order kinetic model parameters for MO and BPB adsorption at 295K.

| Lagergren pseudo second-order kinetics | Calculated $q_e$ (mg/g) | $k_2$ (h g/mg) | Measured $q_e$ (mg/g) | $h^a$ (h g/mg) | $R^2$ |
|---|---|---|---|---|---|
| BPB | 2.334812 | 0.346769168 | 1.98378727 | 1.89035917 | 0.995 |
| MO | 2.3668639 | 1.00397216 | 2.200404334 | 5.62429696 | 0.999 |

$^a$Initial adsorption rate $h = k_2 q_e^2$.

The values represented in Table 4 show that the rate constant ($k_2$) for the removal of BPB is higher than for MO. However, the functionalized asphaltene adsorbs a larger amount of MO at the longer periods of time (FIG. 7, Table 4). The adsorption capacity of MO is thus found to be larger than that of BPB. The rationale for such difference could be attributed to the lower effective ionic radii of BPB than that of MO and differences in the affinity of phosphonate motifs in the adsorbent for the dye [J. A. Dean, Lange's Handbook of Chemistry, 15$^{th}$ ed., McGraw-Hill, 1998—incorporated herein by reference in its entirety]. The results revealed that the adsorbent is an efficient adsorbent for removing both MO and BPB molecules from aqueous solutions.

EXAMPLE 11

Figure 9:
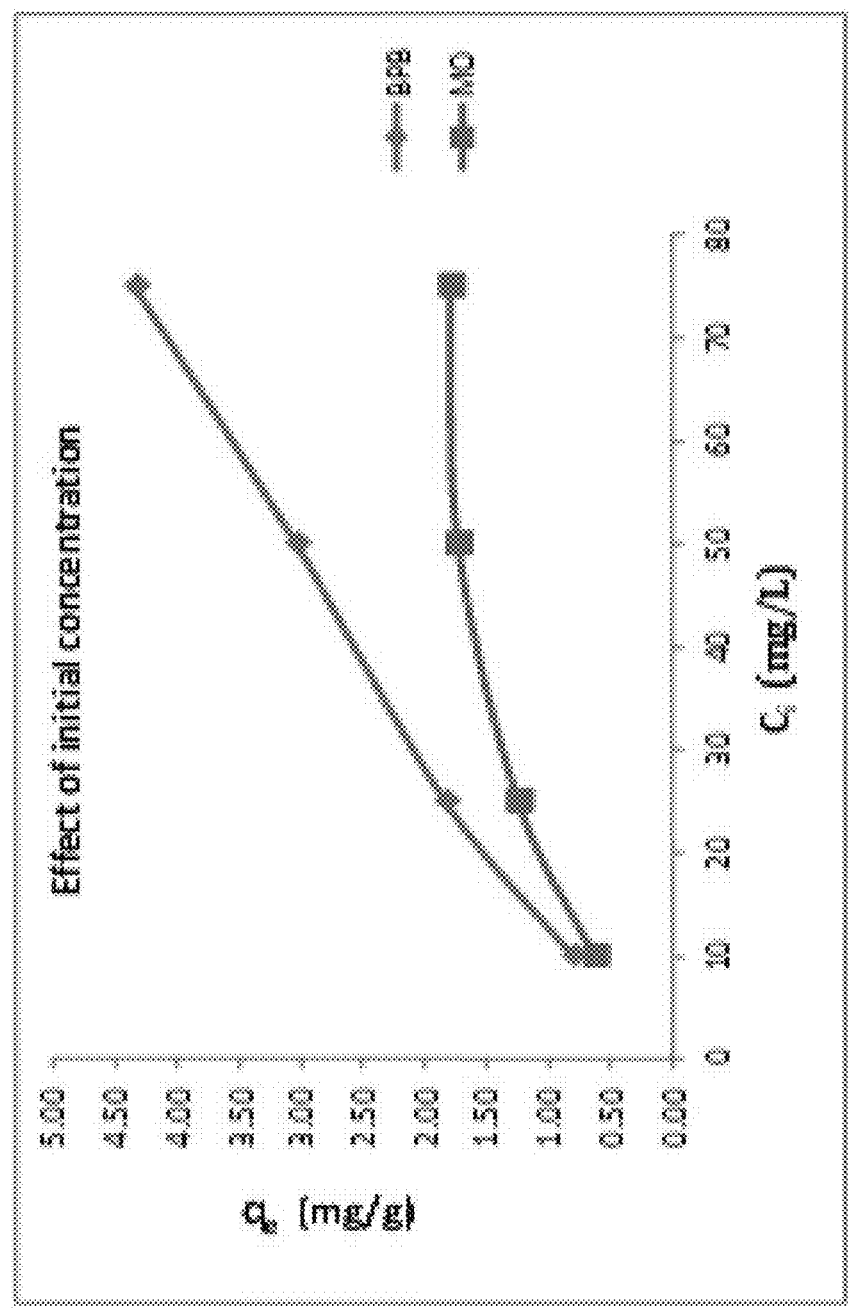
FIG. 9 shows the effect of initial concentration on the adsorption capacity of a functionalized asphaltene adsorbent at pH X for BPB and pH Y for MO, for 7 h and at 25° C.

Effect of Initial Concentration on the Adsorption of Methyl Orange and Bromophenol Blue The adsorption capacity of the functionalized asphaltene increases with increasing concentrations of MO and BPB dyes, as shown in FIG. 9.

EXAMPLE 12

Figure 10:
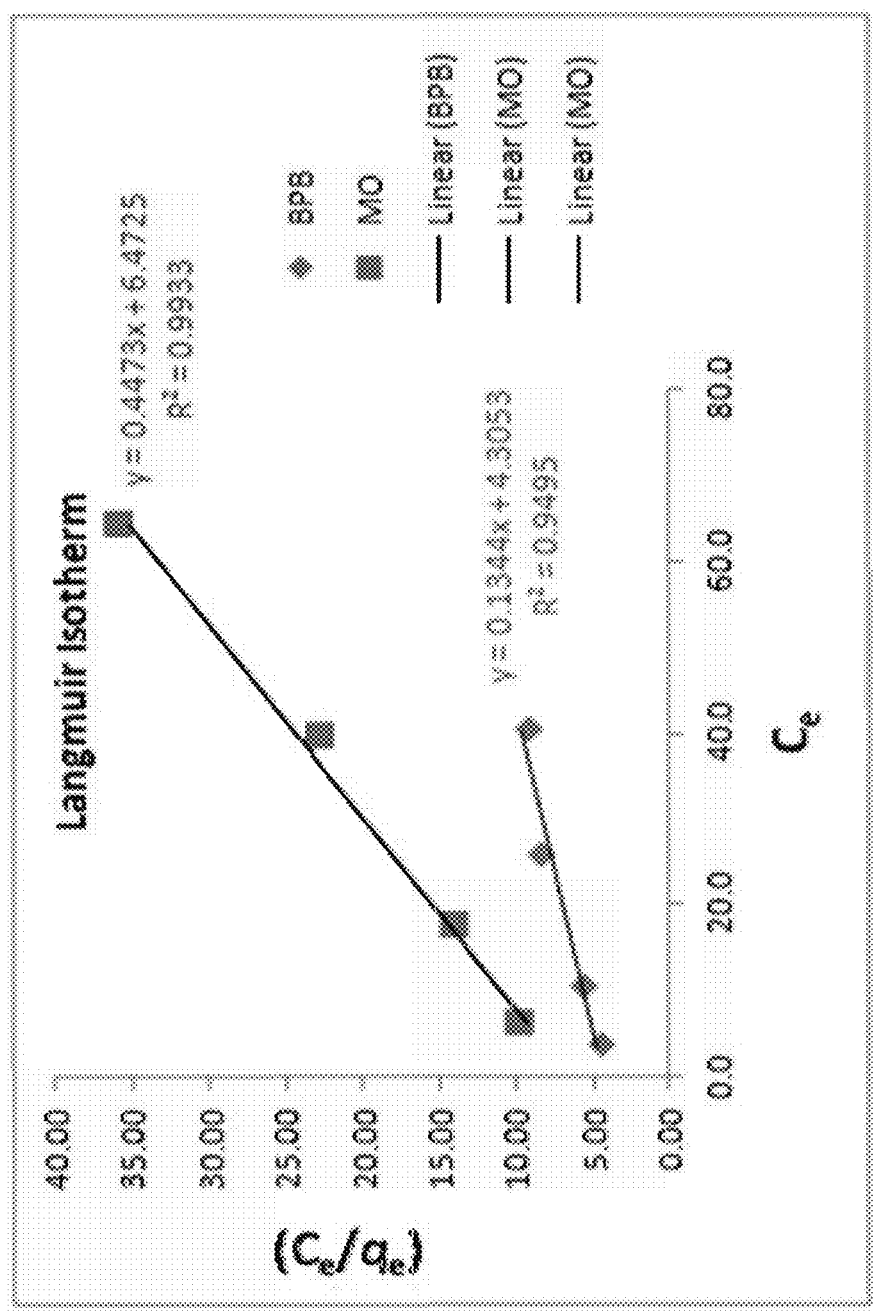
FIG. 10 shows the Langmuir isotherm model adsorption curve of MO and BPB on a functionalized asphaltene adsorbent.

Langmuir, Freundlich and Temkin Isotherm Models of MO and BPB Adsorption on the Functionalized Asphaltene The Langmuir isotherm is based on the assumptions that on structurally homogeneous adsorbent, all adsorption sites are energetically equivalent and identical and that the intermolecular force decreases rapidly with distance. The Langmuir isotherm therefore follows the mechanism as a monolayer adsorption on the surface of the polymer. The Langmuir constants and adsorption capacities are calculated by linearized Langmuir isotherm Eq. (4) as follows:

$$\frac{C_e}{q_e} = \frac{C_e}{Q_m} - \frac{1}{Q_m b} \qquad \text{Eq. (4)}$$

where $q_e$ is milligram of metal adsorbed per gram of the adsorbent; $C_e$ is the metal residual concentration in solution at equilibrium, $Q_m$ is the maximum specific uptake corresponding to the site saturation and b is the ratio of adsorption and desorption rates, the Langmuir constant [A. Cabeza, X. Ouyang, C. V. K. Sharma, M. A. G. Aranda, S. Bruque, A. Clearfield, Complexes Formed between Nitrilotris (methylenephosphonic aCod) and M$^{2+}$ Transition Metals: Isostructural Organic—Inorganic Hybrids, Inorg. Chem. 41 (2002) 2325-2333—incorporated herein by reference in its entirety]. FIG. 10 represents the plot of $C_e/q_e$ versus $C_e$.

On the other hand, the Freundlich isotherm model describes heterogeneous adsorption systems with uniform energy. The model is expressed by Eq. 5 and Eq. 6:

$$q_e = k_f C_e^{1/n} \qquad \text{Eq. (5)}$$

$$\log q_e = \log k_f + \frac{1}{n} \log C_e \qquad \text{Eq. (6)}$$

where $q_e$ and $C_e$ are the equilibrium concentrations of metal ions on the adsorbed and the liquid phase, respectively; $k_f$ and n represent the Freundlich constants, which can be calculated from the slope and intercept of FIG. 11 which shows the plot of log $q_e$ versus log $C_e$.

The Temkin isotherm equation suggests that owing to adsorbent-adsorbate interactions, the heat of adsorption of molecules in layer decreases linearly with coverage, and the adsorption is characterized by a uniform distribution of the bonding energies. The Temkin isotherm can be expressed by Eq. 7:

$$q_e = \frac{RT}{b} \ln(AC_e) \qquad \text{Eq. (7)}$$

and can be linearized as Eq. (8):

$$q_e = B \ln A + B \ln C_e \qquad \text{Eq. (8)}$$

where B Corresponds to the adsorption potential of the adsorbent (kJ/mol), A is the Temkin isotherm constant (L/g). The plot of $q_e$ versus $\ln C_e$ of FIG. 12 is used to calculate the Temkin isotherm constants A and B.

Figure 11:
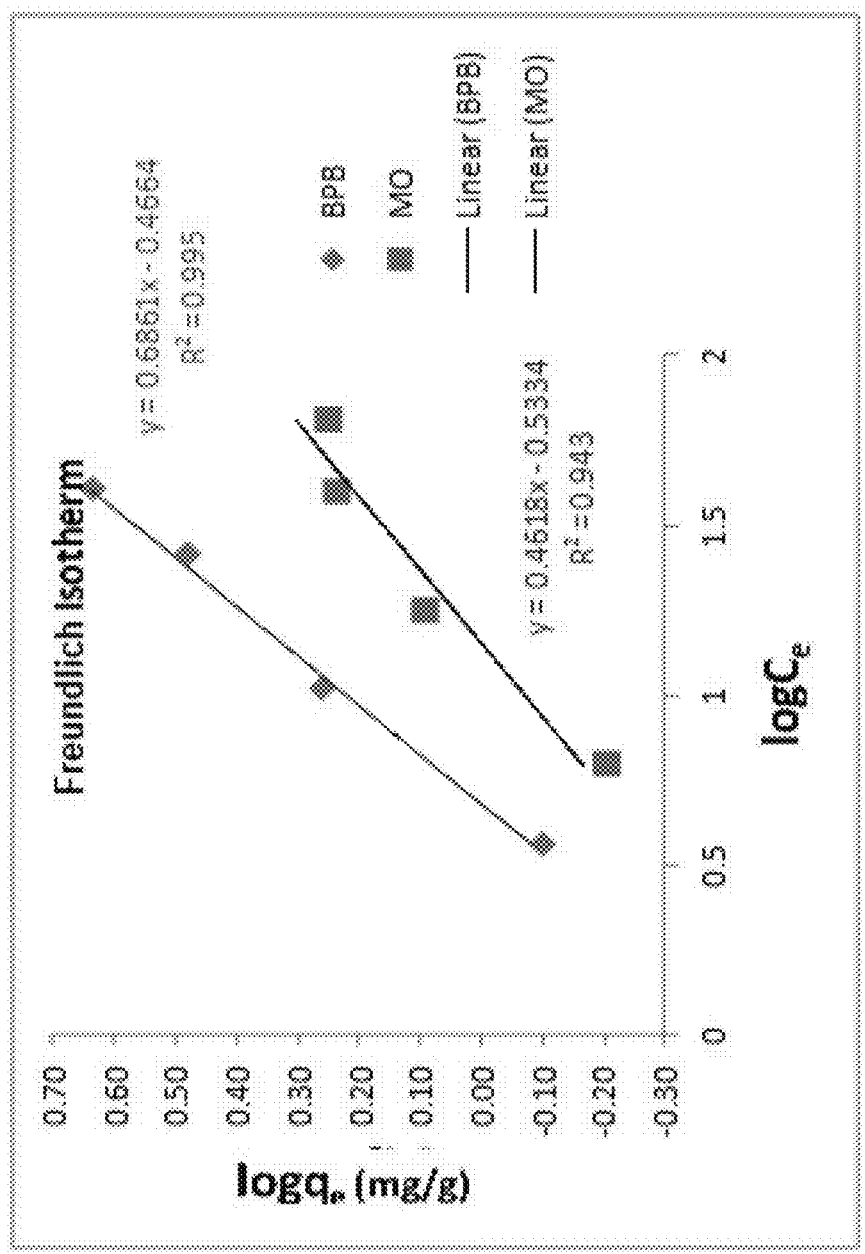
FIG. 11 shows the Freundlich isotherm model adsorption curve of MO and BPB on a functionalized asphaltene adsorbent.
Figure 12:
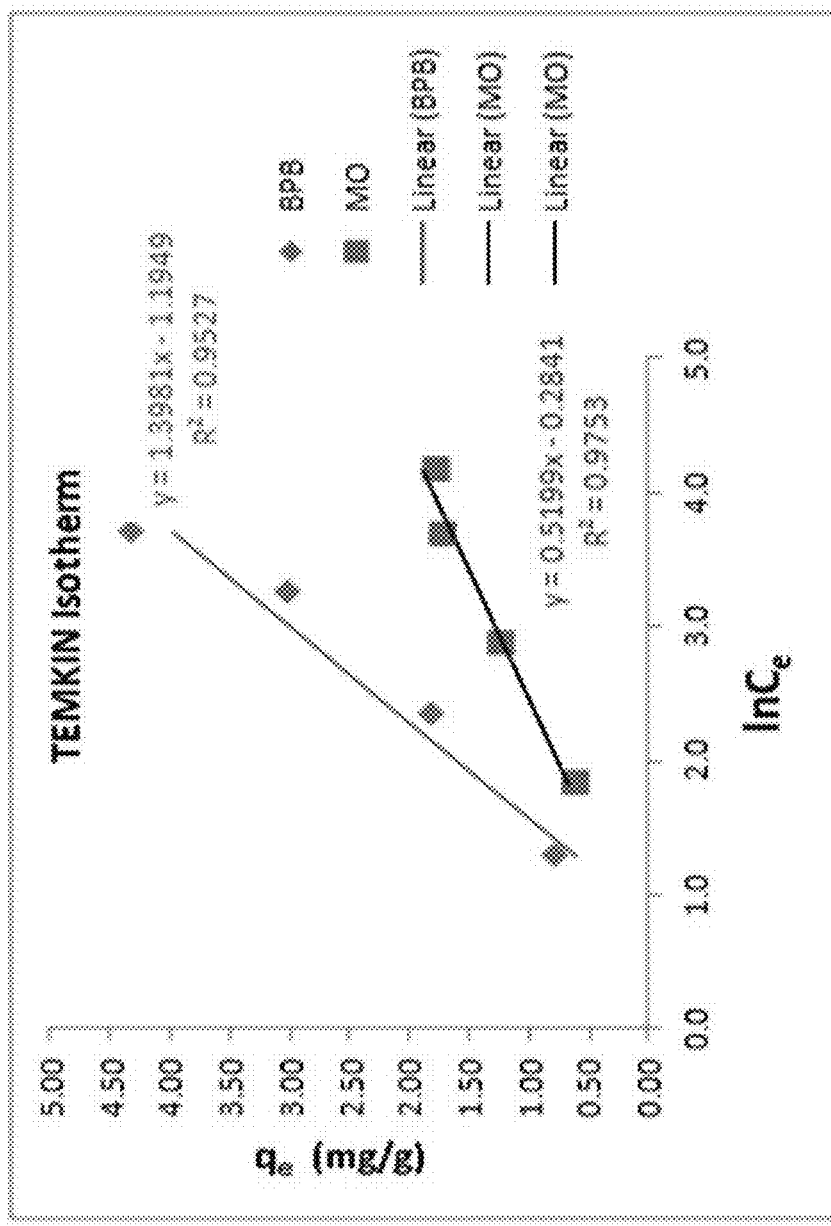
FIG. 12 shows the Temkin isotherm model adsorption curve of MO and BPB on a functionalized asphaltene adsorbent.

FIGS. 10, 11 and 12 illustrate that the adsorption of both MO ad BPB ions by adsorbent fitted well the Langmuir, Freundlich and Temkin isotherm models, thereby implying that the adsorption may occur as a monolayer as well as a heterogeneous surface adsorption. The Langmuir, Freundlich and Temkin isotherm model constants are given in Tables 5, 6 and 7, respectively.

TABLE 5

Langmuir isotherm model constants for MO and BPB adsorption.

| Dye | $Q_m$ (mmol/g) | B (dm³/mmol) | $R^2$ |
|---|---|---|---|
| BPB | 7.440 | 0.031 | 0.95 |
| MO | 2.236 | 0.069 | 0.99 |

TABLE 6

Freundlich isotherm model constants for MO and BPB adsorption.

| Dye | n | $k_f$ | $R^2$ |
|---|---|---|---|
| BPB | 1.458 | 0.342 | 0.995 |
| MO | 2.165 | 0.293 | 0.943 |

TABLE 7

Temkin isotherm model constants for MO and BPB adsorption.

| Dye | B | A | $R^2$ |
|---|---|---|---|
| BPB | 1.3981 | 0.425 | 0.953 |
| MO | 0.5199 | 0.579 | 0.975 |

For the Langmuir isotherm model, separation factor or equilibrium parameter ($R_L$) can be used to describe the favorability of adsorption on the polymer surface by Eq. (9):

$$R_L = \frac{1}{(1 + bC_0)} \qquad \text{Eq. (9)}$$

where $C_o$ is the initial dye concentration and b is the Langmuir equilibrium constant. A favorable adsorption is indicated when the $R_L$ value is between $0 < R_L < 1$, whereas the $R_L$ values outside the range describes an unfavorable adsorption [J. Liu, Y. Ma, Y. Zhang, G. Shao, Novel negatively charged hybrids. 3. Removal of BPB from aqueous solution using zwitterionic hybrid polymers as adsorbent, J. Hazard. Mater. 173 (2010) 438-44—incorporated herein by reference in its entirety].

The $R_L$ values for the adsorption of both dye compounds are given in Table 8, which reveals that $R_L$ values fall in the preferred region ($0 < R_L < 1$). The results thus declare that adsorbent is a promising adsorbent for the removal of heavy metal ions in aqueous solutions.

TABLE 8

The $R_L$ values based on the Langmuir isotherm model.

| $C_i$ (mg/dm³) | $R_L$ value BPB | $R_L$ value MO |
|---|---|---|
| 10 | 0.7621 | 0.5913 |
| 25 | 0.5617 | 0.3666 |
| 50 | 0.3905 | 0.2244 |
| 75 | 0.2993 | 0.1617 |

EXAMPLE 13

Effect of pH and Temperature on Adsorption

Figure 13:
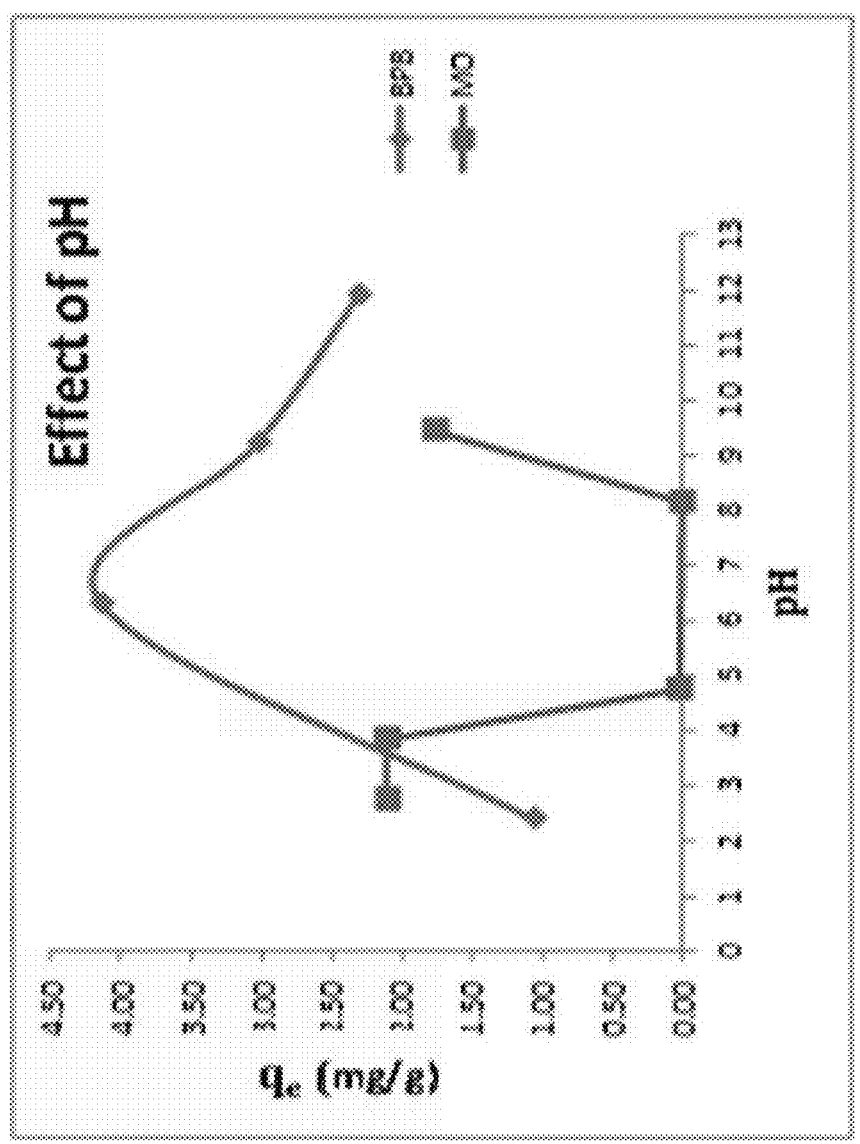
FIG. 13 illustrates the pH dependence of dye uptake by a functionalized asphaltene adsorbent.

Adsorption experiments were performed at various pH values ranging between 2.5-11.0 by using acetate buffer, to find out the effect of pH on uptake of BPB and MO ions. The optimum pH was found to be 6.3 for BPB and 2.7 for MO. pH has a very strong effect on the adsorption capacities, as can be seen in FIG. 13. The adsorption of MO at pH 7 is almost zero while it is 2.20 mg/g at 2.7. Therefore, adsorption of MO by the functionalized asphaltene has to be done between pH 2-3 while desorption will be effective below pH 6-7. Hence, charging and discharging of metal ions is pH controlled.

Figure 14:
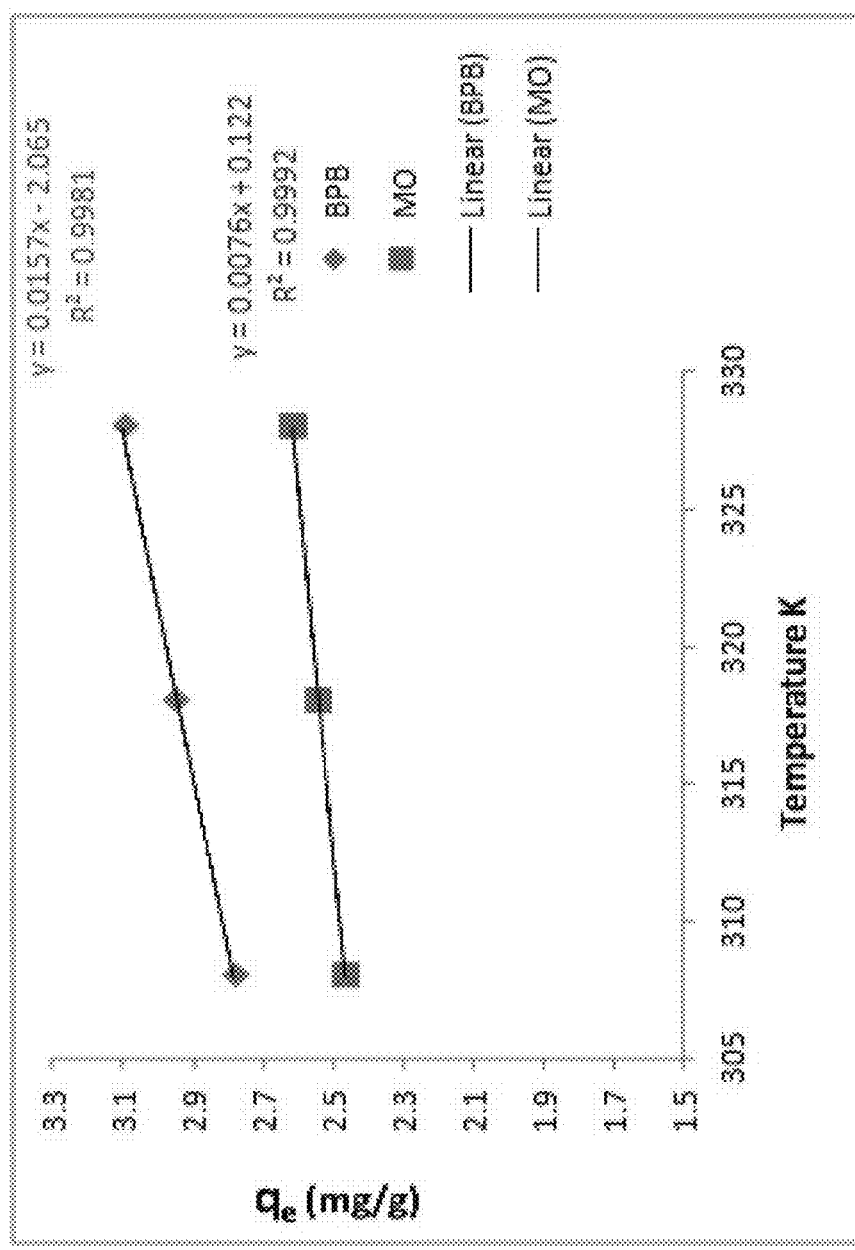
FIG. 14 shows the effect of temperature on the adsorption capacity of a functionalized asphaltene adsorbent.

Adsorption experiments were also performed to obtain the thermodynamic parameters, and the results are illustrated in FIG. 14. As can be seen from the figure, the adsorption capacity increases when the temperature is increased, suggesting that the adsorption process is endothermic.

Figure 15:
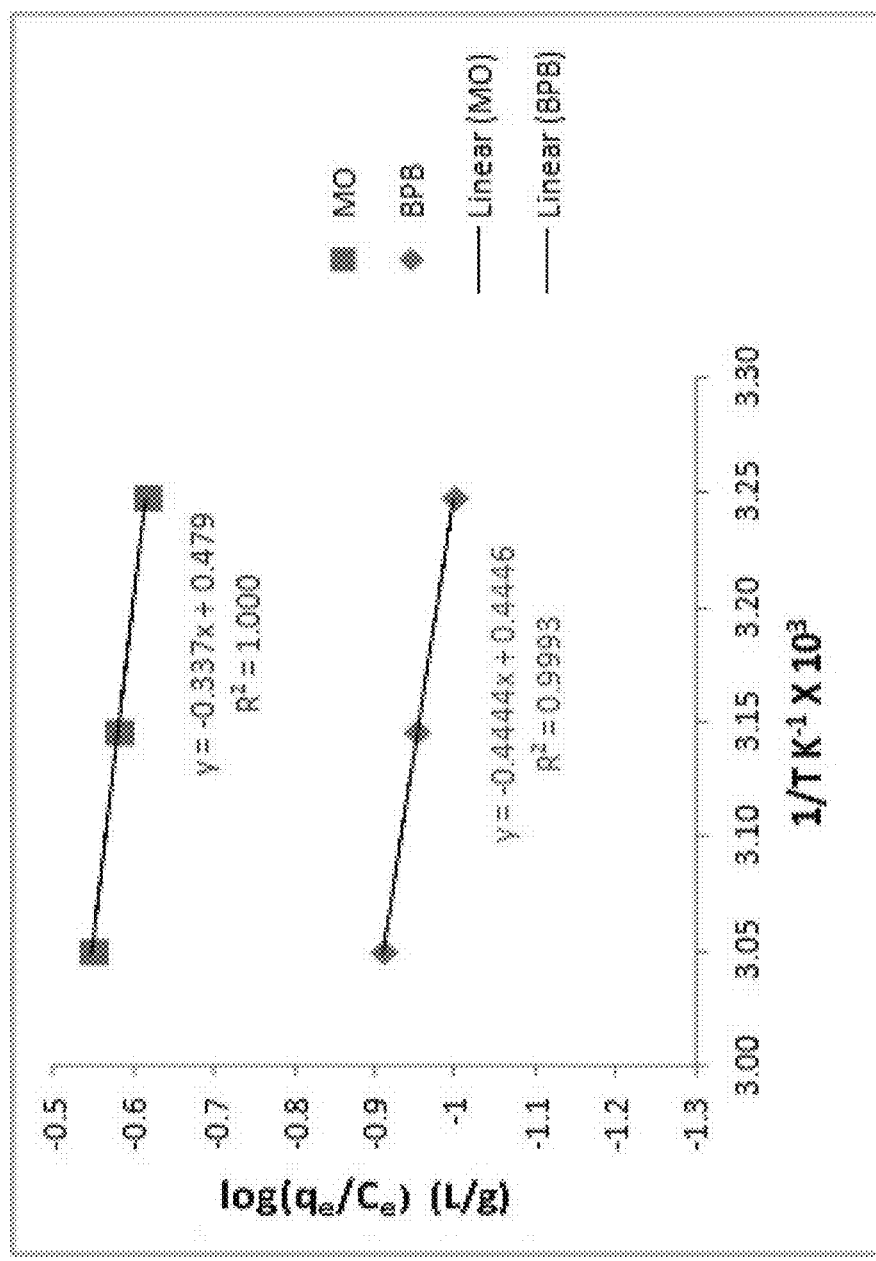
FIG. 15 is a Vant-Hoff's plot for adsorption of MO and BPB on a functionalized asphaltene adsorbent.

A plot of log ($q_e/C_e$) versus 1/T is displayed in FIG. 15. The thermodynamic parameters ΔG, ΔH and ΔS were calculated using Vant-Hoff equation (Eq. (10)), and are tabulated in Table 9 [R. Coş kun, C. Soykan, M. Saçak, Removal of some heavy metal ions from aqueous solution by adsorption using poly(ethylene terephthalate)-g-itaConic aCod/ acrylamide fiber, React. Funct. Polym. 66 (2006) 599-608; A. Ramesh, H. Hasegawa, T. Maki, K. Ueda, Adsorption of inorganic and organic arsenic from aqueous solutions by polymeric Al/Fe modified montmorillonite, Sep. Purif. Technol. 56 (2007) 90-100—each incorporated herein by reference in its entirety]. The negative ΔG values ascertain the spontaneity of the adsorption process.

$$\log\left(\frac{q_e}{C_e}\right) = -\frac{\Delta H}{2.303\, RT} + \frac{\Delta S}{2.303\, R} \qquad \text{Eq. (10)}$$

TABLE 9

Thermodyanamic data for BPB and MO adsorption.

| Dye | Temperature (K) | ΔG (kJ/mol) | ΔH (kJ/mol) | ΔS (kJ/mol) | $R^2$ |
|---|---|---|---|---|---|
| BPB | 295 | −11.020 | +8.509 | 8.513 | 0.9993 |
| MO | 295 | −9.166 | +6.460 | 9.173 | 1.000 |

As the temperature increases the ΔG values become more negative thereby indicating that the adsorption is more favorable at higher temperatures. Favorable adsorption at higher temperatures is attributed to the greater swelling of the adsorbent and increased diffusion of metal ions into the adsorbent. The positive values of ΔH certify that the adsorption is an endothermic process. In addition, it can be found in Table 9 that the ΔS values are positive, suggesting that the randomness increased during adsorption of metal ions as a result of release of water molecules from the large hydration shells of the metal ions.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method for removing a dye compound from an aqueous sample, comprising:
   contacting the aqueous sample with a functionalized asphaltene to adsorb the dye compound onto the functionalized asphaltene, wherein the functionalized asphaltene comprises:
   10-35% by weight of elemental oxygen per total weight of the functionalized asphaltene;
   3-10% by weight of elemental nitrogen per total weight of the functionalized asphaltene; and
   3-10% by weight of elemental sulfur per total weight of the functionalized asphaltene;
   wherein the functionalized asphaltene is obtained by refluxing a petroleum asphaltene with an acid, and
   wherein the functionalized asphaltene has at least one active group selected from the group consisting of an amine group, a nitro group, a carbonyl group, a carboxylic group and a hydroxyl group covalently bonded to an asphaltene core.

2. The method of claim 1, wherein the functionalized asphaltene has an adsorption capacity of 1-5 mg of the dye compound per g of the functionalized asphaltene.

3. The method of claim 1, wherein the aqueous sample is contacted with functionalized asphaltene for 2-7 h.

4. The method of claim 1, wherein the aqueous sample is contacted with 1-10 mg/ml of functionalized asphaltene.

5. The method of claim 1, wherein the dye compound is bromophenol blue and the aqueous sample is contacted with the functionalized asphaltene at pH 4-9.

6. The method of claim 1, wherein the dye compound is methyl orange and the aqueous sample is contacted with the functionalized asphaltene at pH of 2.5-4.

7. The method of claim 5, further comprising:
   desorbing the bromophenol blue from the functionalized asphaltene at a pH of lower than 4 or higher than 9.

8. The method of claim 6, further comprising:
   desorbing the methyl orange from the functionalized asphaltene at a pH of higher than 4 and lower than 8.

9. The method of claim 1, wherein the functionalized asphaltene has an average particle size of 10-20 nm.

10. The method of claim 1, wherein the functionalized asphaltene has a particle size distribution of 0.5-100 nm with at least 60% of the particles having a particle size of 10-20 nm.

11. The method of claim 1, wherein the functionalized asphaltene has a specific surface area of no higher than 10 $m^2/g$.

12. The method of claim 1, wherein the functionalized asphaltene has an adsorption average pore width of 1-10 nm.

13. The method of claim 1, wherein the petroleum asphaltene is refluxed with the acid at 70-90° C. for 1-2 h.

14. The method of claim 1, wherein the acid is 70% v/v concentrated nitric acid.

* * * * *